United States Patent
Steinmiller et al.

(10) Patent No.: US 9,827,564 B2
(45) Date of Patent: Nov. 28, 2017

(54) FLUIDIC SYSTEMS AND METHODS FOR ANALYSES

(71) Applicant: OPKO Diagnostics, LLC, Woburn, MA (US)

(72) Inventors: David Steinmiller, Mountain View, CA (US); Vincent Linder, Tewksbury, MA (US)

(73) Assignee: OPKO Diagnostics, LLC, Woburn, MA (US)

(*) Notice: Subject to any disclaimer, the term of this patent is extended or adjusted under 35 U.S.C. 154(b) by 0 days.

(21) Appl. No.: 15/196,975

(22) Filed: Jun. 29, 2016

(65) Prior Publication Data
US 2016/0305937 A1 Oct. 20, 2016

Related U.S. Application Data

(60) Continuation of application No. 14/316,069, filed on Jun. 26, 2014, which is a continuation of application
(Continued)

(51) Int. Cl.
*B01L 3/00* (2006.01)
*G01N 31/16* (2006.01)
(Continued)

(52) U.S. Cl.
CPC ....... *B01L 3/502707* (2013.01); *B01L 3/5027* (2013.01); *B01L 3/502715* (2013.01);
(Continued)

(58) Field of Classification Search
CPC ............... G01N 31/16; A61J 1/06; B01L 3/00
(Continued)

(56) References Cited

U.S. PATENT DOCUMENTS 3,735,640 A 5/1973 Chizhov et al.
4,318,994 A 3/1982 Meyer et al.
(Continued)

FOREIGN PATENT DOCUMENTS

DE 198 16 224 10/1998
EP 0 110 771 B1 3/1988
(Continued)

OTHER PUBLICATIONS

U.S. Appl. No. 14/316,069, filed Jun. 26, 2014, Steinmiller et al.
(Continued)

*Primary Examiner* — Brian J Sines
(74) *Attorney, Agent, or Firm* — Wolf, Greenfield & Sacks, P.C.

(57) ABSTRACT

Fluidic systems and methods for analysis are provided. In some embodiments, systems and methods for improved measurement of absorbance/transmission through fluidic systems are described. Specifically, in one set of embodiments, optical elements are fabricated on one side of a transparent fluidic device opposite a series of fluidic channels. The optical elements may guide incident light passing through the device such that most of the light is dispersed away from specific areas of the device, such as intervening portions between the fluidic channels. By decreasing the amount of light incident upon these intervening portions, the amount of noise in the detection signal can be decreased when using certain optical detection systems.

32 Claims, 19 Drawing Sheets

Related U.S. Application Data

No. 13/898,028, filed on May 20, 2013, now Pat. No. 8,802,029, which is a division of application No. 13/490,055, filed on Jun. 6, 2012, now Pat. No. 8,480,975, which is a continuation of application No. 12/698,451, filed on Feb. 2, 2010, now Pat. No. 8,221,700.

(60) Provisional application No. 61/149,253, filed on Feb. 2, 2009.

(51) Int. Cl.

| | | |
|---|---|---|
| *A61J 1/06* | (2006.01) | |
| *G01N 21/03* | (2006.01) | |
| *G01N 21/59* | (2006.01) | |
| *G01N 33/53* | (2006.01) | |
| *G01N 33/543* | (2006.01) | |
| *G01N 33/545* | (2006.01) | |
| *G01N 33/574* | (2006.01) | |

(52) U.S. Cl.
CPC .. *C12Y 304/21077* (2013.01); *G01N 21/0303* (2013.01); *G01N 21/59* (2013.01); *G01N 33/53* (2013.01); *G01N 33/545* (2013.01); *G01N 33/54366* (2013.01); *G01N 33/54373* (2013.01); *G01N 33/57488* (2013.01); *B01L 2200/12* (2013.01); *B01L 2300/04* (2013.01); *B01L 2300/0627* (2013.01); *B01L 2300/0654* (2013.01); *B01L 2300/0861* (2013.01); *B01L 2300/12* (2013.01); *G01N 2333/96455* (2013.01); *Y10T 436/11* (2015.01)

(58) Field of Classification Search
USPC ... 422/68.1, 503, 82.05, 82.08, 82.09, 82.11, 422/502, 551, 552, 553, 554, 559; 436/43, 63, 164, 171, 172, 524, 518
See application file for complete search history.

(56) References Cited

U.S. PATENT DOCUMENTS

| | | | |
|---|---|---|---|
| 4,517,302 A | 5/1985 | Saros | |
| 4,871,233 A | 10/1989 | Sheiman | |
| 4,918,025 A | 4/1990 | Grenner | |
| 4,963,498 A | 10/1990 | Hillman et al. | |
| 5,051,237 A | 9/1991 | Grenner et al. | |
| 5,219,762 A | 6/1993 | Katamine et al. | |
| 5,234,813 A | 8/1993 | McGeehan et al. | |
| 5,268,147 A | 12/1993 | Zabetakis et al. | |
| 5,286,454 A | 2/1994 | Nilsson et al. | |
| 5,376,252 A | 12/1994 | Ekström et al. | |
| 5,478,751 A | 12/1995 | Oosta et al. | |
| 5,486,335 A | 1/1996 | Wilding et al. | |
| 5,516,639 A * | 5/1996 | Tindall et al. | 435/7.4 |
| 5,571,410 A | 11/1996 | Swedberg et al. | |
| 5,585,069 A | 12/1996 | Zanzucchi et al. | |
| 5,599,503 A | 2/1997 | Manz et al. | |
| 5,614,372 A * | 3/1997 | Lilja et al. | 435/7.23 |
| 5,635,358 A | 6/1997 | Wilding et al. | |
| 5,637,469 A | 6/1997 | Wilding et al. | |
| 5,638,828 A | 6/1997 | Lauks et al. | |
| 5,672,480 A | 9/1997 | Dowell et al. | |
| 5,726,026 A | 3/1998 | Wilding et al. | |
| 5,731,212 A | 3/1998 | Gavin et al. | |
| 5,840,501 A * | 11/1998 | Allard et al. | 435/7.4 |
| 5,842,787 A | 12/1998 | Koph-Sill et al. | |
| 5,866,345 A | 2/1999 | Wilding et al. | |
| 5,876,675 A | 3/1999 | Kennedy | |
| 5,923,481 A | 7/1999 | Skidmore et al. | |
| 5,939,533 A | 8/1999 | Lilja et al. | |
| 5,942,443 A | 8/1999 | Parce et al. | |
| 5,955,028 A | 9/1999 | Chow | |
| 5,957,579 A | 9/1999 | Kopf-Sill et al. | |
| 6,019,944 A | 2/2000 | Buechler | |
| 6,042,709 A | 3/2000 | Parce et al. | |
| 6,046,056 A | 4/2000 | Parce et al. | |
| 6,100,541 A | 8/2000 | Nagle et al. | |
| 6,103,199 A | 8/2000 | Bjornson et al. | |
| 6,136,272 A | 10/2000 | Weigl et al. | |
| 6,146,489 A | 11/2000 | Wirth | |
| 6,146,589 A | 11/2000 | Chandler | |
| 6,168,948 B1 | 1/2001 | Anderson et al. | |
| 6,176,962 B1 | 1/2001 | Soane et al. | |
| 6,184,029 B1 | 2/2001 | Wilding et al. | |
| 6,186,660 B1 | 2/2001 | Kopf-Sill et al. | |
| 6,207,369 B1 | 3/2001 | Wohlstadter et al. | |
| 6,209,928 B1 | 4/2001 | Benett et al. | |
| 6,214,560 B1 | 4/2001 | Yguerabide et al. | |
| 6,238,538 B1 | 5/2001 | Parce et al. | |
| 6,241,560 B1 | 6/2001 | Furusawa et al. | |
| 6,251,343 B1 | 6/2001 | Dubrow et al. | |
| 6,274,337 B1 | 8/2001 | Parce et al. | |
| 6,296,020 B1 | 10/2001 | McNeely et al. | |
| 6,319,476 B1 | 11/2001 | Victor et al. | |
| 6,331,439 B1 | 12/2001 | Cherukuri et al. | |
| 6,333,200 B1 | 12/2001 | Kaler et al. | |
| 6,361,958 B1 | 3/2002 | Shieh et al. | |
| 6,413,782 B1 | 7/2002 | Parce et al. | |
| 6,416,642 B1 | 7/2002 | Alajoki et al. | |
| 6,429,025 B1 | 8/2002 | Parce et al. | |
| 6,432,720 B2 | 8/2002 | Chow | |
| 6,479,299 B1 | 11/2002 | Parce et al. | |
| 6,488,872 B1 | 12/2002 | Beebe et al. | |
| 6,488,894 B1 | 12/2002 | Miethe et al. | |
| 6,488,896 B2 | 12/2002 | Weigl et al. | |
| 6,495,104 B1 | 12/2002 | Unno et al. | |
| 6,498,353 B2 | 12/2002 | Nagle et al. | |
| 6,499,499 B2 | 12/2002 | Dantsker et al. | |
| 6,536,477 B1 | 3/2003 | O'Connor et al. | |
| 6,551,841 B1 | 4/2003 | Wilding et al. | |
| 6,557,427 B2 | 5/2003 | Weigl et al. | |
| 6,558,945 B1 | 5/2003 | Kao | |
| 6,585,939 B1 | 7/2003 | Dapprich | |
| 6,610,499 B1 | 8/2003 | Fulwyler et al. | |
| 6,613,512 B1 | 9/2003 | Kopf-Sill et al. | |
| 6,613,525 B2 | 9/2003 | Nelson et al. | |
| 6,620,625 B2 | 9/2003 | Wolk et al. | |
| 6,632,619 B1 | 10/2003 | Harrison et al. | |
| 6,638,482 B1 | 10/2003 | Ackley et al. | |
| 6,656,430 B2 | 12/2003 | Sheppard, Jr. et al. | |
| 6,660,367 B1 | 12/2003 | Yang et al. | |
| 6,669,831 B2 | 12/2003 | Chow et al. | |
| 6,705,357 B2 | 3/2004 | Jeon et al. | |
| 6,709,869 B2 | 3/2004 | Mian et al. | |
| 6,710,870 B1 | 3/2004 | Marowsky et al. | |
| 6,716,620 B2 | 4/2004 | Bashir et al. | |
| 6,729,352 B2 | 5/2004 | O'Connor et al. | |
| 6,742,661 B1 * | 6/2004 | Schulte et al. | 210/511 |
| 6,759,662 B1 | 7/2004 | Li | |
| 6,761,962 B2 | 7/2004 | Bentsen et al. | |
| 6,780,584 B1 | 8/2004 | Edman et al. | |
| 6,794,197 B1 | 9/2004 | Indermuhle et al. | |
| 6,818,184 B2 | 11/2004 | Fulwyler et al. | |
| 6,827,095 B2 | 12/2004 | O'Connor et al. | |
| 6,828,143 B1 | 12/2004 | Bard | |
| 6,830,936 B2 | 12/2004 | Anderson et al. | |
| 6,858,185 B1 | 2/2005 | Kopf-Sill et al. | |
| 6,875,403 B2 | 4/2005 | Liu et al. | |
| 6,878,271 B2 | 4/2005 | Gilbert et al. | |
| 6,878,755 B2 | 4/2005 | Singh et al. | |
| 6,906,797 B1 | 6/2005 | Kao et al. | |
| 6,949,377 B2 * | 9/2005 | Ho | 435/287.1 |
| 6,953,550 B2 | 10/2005 | Sheppard, Jr. et al. | |
| 6,982,787 B1 | 1/2006 | Wapner et al. | |
| 6,989,128 B2 | 1/2006 | Alajoki et al. | |
| 7,005,292 B2 | 2/2006 | Wilding et al. | |
| 7,015,046 B2 | 3/2006 | Wohlstadter et al. | |
| 7,018,830 B2 | 3/2006 | Wilding et al. | |
| 7,019,831 B2 | 3/2006 | Grossman et al. | |
| 7,027,683 B2 | 4/2006 | O'Connor et al. | |
| 7,046,357 B2 | 5/2006 | Weinberger et al. | |

(56) References Cited

U.S. PATENT DOCUMENTS

| | | | |
|---|---|---|---|
| 7,067,263 B2 | 6/2006 | Parce et al. |
| 7,087,148 B1 | 8/2006 | Blackburn et al. |
| 7,091,048 B2 | 8/2006 | Parce et al. |
| 7,157,053 B2 | 1/2007 | Hahn et al. |
| 7,182,371 B1 | 2/2007 | Renzi |
| 7,202,945 B2* | 4/2007 | Erlbacher et al. ............ 356/246 |
| 7,262,838 B2 | 8/2007 | Fritz |
| 7,262,859 B2 | 8/2007 | Larson et al. |
| 7,276,330 B2 | 10/2007 | Chow et al. |
| 7,475,916 B2 | 1/2009 | Muller et al. |
| 7,513,535 B2 | 4/2009 | Charles et al. |
| 7,515,261 B2 | 4/2009 | Sharma |
| 7,524,462 B2 | 4/2009 | Leonard et al. |
| 7,598,091 B2 | 10/2009 | Wang |
| 7,605,003 B2 | 10/2009 | Chan et al. |
| 7,611,616 B2 | 11/2009 | Cohen et al. |
| 7,736,890 B2 | 6/2010 | Babak et al. |
| 7,763,856 B2 | 7/2010 | Kiesel et al. |
| 7,799,558 B1 | 9/2010 | Dultz |
| 7,863,037 B1 | 1/2011 | Dultz |
| 7,872,104 B2 | 1/2011 | Pettersson et al. |
| 7,894,071 B2 | 2/2011 | Frese et al. |
| 7,934,519 B2 | 5/2011 | Zantl |
| 7,951,529 B2 | 5/2011 | Li et al. |
| 7,952,705 B2 | 5/2011 | Shen et al. |
| 8,000,762 B2 | 8/2011 | Calasso et al. |
| 8,030,057 B2 | 10/2011 | Linder et al. |
| 8,173,433 B2 | 5/2012 | Folkman et al. |
| 8,202,492 B2 | 6/2012 | Linder et al. |
| 8,221,700 B2 | 7/2012 | Steinmiller et al. |
| 8,282,896 B2 | 10/2012 | Facer et al. |
| 8,329,118 B2 | 12/2012 | Padmanabhan et al. |
| 8,389,272 B2 | 3/2013 | Linder et al. |
| 8,409,527 B2 | 4/2013 | Linder et al. |
| 8,475,737 B2 | 7/2013 | Linder et al. |
| 8,480,975 B2 | 7/2013 | Steinmiller et al. |
| 8,574,924 B2 | 11/2013 | Sia et al. |
| 8,580,569 B2 | 11/2013 | Linder et al. |
| 8,591,829 B2 | 11/2013 | Taylor et al. |
| 8,633,013 B2 | 1/2014 | Kaiser et al. |
| 8,765,062 B2 | 7/2014 | Linder et al. |
| 8,802,029 B2 | 8/2014 | Steinmiller et al. |
| 8,802,445 B2 | 8/2014 | Linder et al. |
| 8,808,647 B2* | 8/2014 | Cherubini et al. ............ 422/553 |
| 8,932,523 B2 | 1/2015 | Linder et al. |
| 9,075,047 B2 | 7/2015 | Linder et al. |
| 9,116,124 B2 | 8/2015 | Linder et al. |
| 9,116,148 B2 | 8/2015 | Linder et al. |
| 9,234,888 B2 | 1/2016 | Linder et al. |
| 9,672,329 B2 | 6/2017 | Vickers et al. |
| 2001/0048637 A1 | 12/2001 | Weigl et al. |
| 2002/0001695 A1 | 1/2002 | Tajima et al. |
| 2002/0001818 A1 | 1/2002 | Brock |
| 2002/0019059 A1 | 2/2002 | Chow et al. |
| 2002/0071788 A1 | 6/2002 | Fujii et al. |
| 2002/0092767 A1 | 7/2002 | Bjornson et al. |
| 2002/0135780 A1 | 9/2002 | Budach et al. |
| 2002/0142618 A1 | 10/2002 | Parce et al. |
| 2002/0199094 A1 | 12/2002 | Strand et al. |
| 2003/0012697 A1 | 1/2003 | Hahn et al. |
| 2003/0063851 A1* | 4/2003 | Hillendahl ............ G01N 21/253 385/31 |
| 2003/0082081 A1 | 5/2003 | Fouillet et al. |
| 2003/0103207 A1 | 6/2003 | Kopf-Sill et al. |
| 2003/0118486 A1 | 6/2003 | Zhou et al. |
| 2003/0124623 A1 | 7/2003 | Yager et al. |
| 2003/0138969 A1 | 7/2003 | Jakobsen et al. |
| 2003/0207328 A1 | 11/2003 | Yguerabide et al. |
| 2003/0235816 A1 | 12/2003 | Slawin et al. |
| 2003/0235905 A1 | 12/2003 | Spiecker |
| 2004/0077074 A1 | 4/2004 | Ackley et al. |
| 2004/0101914 A1 | 5/2004 | Pettersson et al. |
| 2004/0115094 A1 | 6/2004 | Gumbrecht et al. |
| 2004/0195728 A1 | 10/2004 | Slomski et al. |
| 2004/0196569 A1 | 10/2004 | Quake et al. |
| 2004/0228771 A1 | 11/2004 | Zhou et al. |
| 2005/0026300 A1 | 2/2005 | Samper et al. |
| 2005/0068526 A1 | 3/2005 | Avrutsky |
| 2005/0118061 A1 | 6/2005 | Mototsu et al. |
| 2005/0118073 A1 | 6/2005 | Facer et al. |
| 2005/0148063 A1 | 7/2005 | Cracauer et al. |
| 2005/0161669 A1 | 7/2005 | Jovanovich et al. |
| 2005/0179901 A1 | 8/2005 | Ostlin et al. |
| 2005/0221281 A1 | 10/2005 | Ho |
| 2005/0238545 A1 | 10/2005 | Parce et al. |
| 2005/0255003 A1 | 11/2005 | Summersgill et al. |
| 2005/0257885 A1 | 11/2005 | Hobbs |
| 2006/0002827 A1 | 1/2006 | Curcio et al. |
| 2006/0013740 A1 | 1/2006 | Berndtsson et al. |
| 2006/0094119 A1 | 5/2006 | Ismagilov et al. |
| 2006/0227328 A1 | 10/2006 | Vanwiggeren et al. |
| 2006/0257992 A1 | 11/2006 | McDevitt et al. |
| 2006/0275852 A1 | 12/2006 | Montagu |
| 2007/0029202 A1 | 2/2007 | Falk-Jordan et al. |
| 2007/0048189 A1 | 3/2007 | Cox et al. |
| 2007/0065954 A1 | 3/2007 | Taya et al. |
| 2007/0202538 A1* | 8/2007 | Glezer et al. ............ 435/7.1 |
| 2007/0298433 A1 | 12/2007 | Sia et al. |
| 2008/0019015 A1 | 1/2008 | Fernandez et al. |
| 2008/0038839 A1 | 2/2008 | Linder et al. |
| 2008/0085219 A1 | 4/2008 | Beebe et al. |
| 2008/0112059 A1 | 5/2008 | Choi et al. |
| 2008/0219616 A1 | 9/2008 | Wimberger-Friedl et al. |
| 2008/0245971 A1 | 10/2008 | Wimberger-Friedl et al. |
| 2008/0248590 A1 | 10/2008 | Gulliksen et al. |
| 2008/0280365 A1 | 11/2008 | Grumann et al. |
| 2008/0286858 A1 | 11/2008 | Cracauer et al. |
| 2009/0019953 A1 | 1/2009 | Bommarito et al. |
| 2009/0084496 A1 | 4/2009 | Fonverne et al. |
| 2009/0190121 A1 | 7/2009 | Hegyi et al. |
| 2009/0290157 A1 | 11/2009 | Dultz et al. |
| 2010/0158756 A1 | 6/2010 | Linder et al. |
| 2010/0196207 A1 | 8/2010 | Steinmiller et al. |
| 2010/0233038 A1 | 9/2010 | Park et al. |
| 2011/0015091 A1 | 1/2011 | Glezer et al. |
| 2012/0022793 A1 | 1/2012 | Barker et al. |
| 2012/0140208 A1 | 6/2012 | Magnusson et al. |
| 2012/0237401 A1 | 9/2012 | Steinmiller et al. |
| 2012/0269701 A1 | 10/2012 | Linder et al. |
| 2013/0157286 A1 | 6/2013 | Linder et al. |
| 2013/0273643 A1 | 10/2013 | Vickers et al. |
| 2014/0023565 A1 | 1/2014 | Taylor et al. |
| 2014/0038166 A1 | 2/2014 | Linder et al. |
| 2014/0038167 A1 | 2/2014 | Linder et al. |
| 2014/0134603 A1 | 5/2014 | Sia et al. |
| 2014/0234180 A1 | 8/2014 | Linder et al. |
| 2015/0086997 A1 | 3/2015 | Linder et al. |
| 2015/0196908 A9 | 7/2015 | Steinmiller et al. |
| 2015/0233901 A1 | 8/2015 | Linder et al. |
| 2015/0343443 A1 | 12/2015 | Linder et al. |
| 2016/0025732 A1 | 1/2016 | Linder et al. |
| 2016/0282349 A1 | 9/2016 | Linder et al. |
| 2016/0305878 A1 | 10/2016 | Steinmiller et al. |
| 2016/0305938 A1 | 10/2016 | Linder et al. |
| 2016/0320394 A1 | 11/2016 | Dong et al. |
| 2017/0089904 A1 | 3/2017 | Dong et al. |
| 2017/0091379 A1 | 3/2017 | Vickers et al. |
| 2017/0091380 A1 | 3/2017 | Vickers et al. |

FOREIGN PATENT DOCUMENTS

| | | |
|---|---|---|
| EP | 0 488 947 | 6/1992 |
| EP | 0 643 307 A1 | 3/1995 |
| EP | 1 054 259 A1 | 11/2000 |
| EP | 1 946 830 A1 | 7/2008 |
| EP | 2 071 026 A1 | 6/2009 |
| JP | 2006-038726 A | 2/2006 |
| JP | 2006-308428 A | 11/2006 |
| JP | 2007-017354 A | 1/2007 |
| WO | WO 91/01003 A | 1/1991 |
| WO | WO 95/26796 | 10/1995 |
| WO | WO 96/14934 | 5/1996 |
| WO | WO 96/15269 | 5/1996 |
| WO | WO 97/06437 A1 | 2/1997 |

(56) References Cited

FOREIGN PATENT DOCUMENTS

| WO | WO 02/22250 A2 | 3/2002 |
|---|---|---|
| WO | WO 03/054513 A2 | 7/2003 |
| WO | WO 2004/022233 A1 | 3/2004 |
| WO | WO 2004/061418 A2 | 7/2004 |
| WO | WO 04/087951 A2 | 10/2004 |
| WO | WO 04/087951 A3 | 10/2004 |
| WO | WO 2004/087951 A2 | 10/2004 |
| WO | WO 2004/105946 A2 | 12/2004 |
| WO | WO 2005/056186 A | 6/2005 |
| WO | WO 2005/056186 A1 | 6/2005 |
| WO | WO 2005/072858 | 8/2005 |
| WO | WO 2006/018044 A1 | 2/2006 |
| WO | WO 2006/056787 A1 | 6/2006 |
| WO | WO 2006/113727 A2 | 10/2006 |
| WO | WO 2007/060523 A1 | 5/2007 |
| WO | WO 2007/077218 A1 | 7/2007 |
| WO | WO 2008/118098 A1 | 10/2008 |
| WO | WO 2008/123112 A1 | 10/2008 |
| WO | WO 2008/137008 A2 | 11/2008 |
| WO | WO 2010/080115 A2 | 7/2010 |
| WO | WO 2013/134179 A2 | 9/2013 |
| WO | WO 2013/172779 A2 | 11/2013 |

OTHER PUBLICATIONS

U.S. Appl. No. 15/196,922, filed Jun. 29, 2016, Steinmiller et al.
PCT/US2008/005577, Apr. 3, 2009, International Search Report and Written Opinion.
PCT/US2008/005577, Oct. 5, 2009, International Preliminary Report on Patentabillity.
PCT/US2010/000286, Jun. 17, 2010, International Search Report and Written Opinion.
PCT/US2010/000286, Mar. 24, 2011, International Preliminary Report on Patentability.
International Search Report and Written Opinion for PCT/US2008/005577 dated Apr. 3, 2009.
International Preliminary Report on Patentability for International Application No. PCT/US2008/005577 dated Oct. 5, 2009.
International Search Report and Written Opinion for PCT/US2010/000286 dated Jun. 17, 2010.
International Preliminary Report on Patentability for International Application No. PCT/US2010/000286 dated Mar. 24, 2011.
Ahn et al., Disposable Smart Lab on a Chip for Point-of-Care Clinical Diagnostics, Proceedings of the IEEE. 2004; 92(1):154-173.
Andersson et al., Micromachined flow-through filter-chamber for chemical reactions on beads. Sensors and Actuators. 2000; B67:203-208.
Atencia et al., Capillary inserts in microcirculatory systems. Lab Chip. Apr. 2006;6(4):575-7. Epub Jan. 20, 2006.
Atencia et al., Steady flow generation in microcirculatory systems. Lab Chip. Apr. 2006;6(4):567-74. Epub Jan. 20, 2006.
Daridon et al., Chemical sensing using an integrated microfluidic system based on the Berthelot reaction. Sensors and Actuators B. 2001;76:235-243.
Dodge et al., Electrokinetically driven microfluidic chips with surface-modified chambers for heterogeneous immunoassays. Anal Chem. Jul. 15, 2001;73(14):3400-9.
Dong et al., Variable-Focus Liquid Microlenses and Microlens Arrays Actuated by Thermoresponsive Hydrogels. Advanced Materials. 2007;19:401-5.
Fredrickson et al., Macro-to-micro interfaces for microfluidic devices. Lab Chip. Dec. 2004;4(6):526-33. Epub Nov. 10, 2004.
Grodzinski et al., A Modular Microfluidic System for Cell Pre-concentration and Genetic Sample Preparation. Biomedical Microdevices. 2003;5(4):303-310.
Jo et al., Three-Dimensional Microchannel Fabrication in PDMS Elastomer. J. Microelectro Sys. 2000;9(1):76-81.
Juncker et al., Autonomous microfluidic capillary system. Anal Chem. Dec. 15, 2002;74(24):6139-44.
Kuswandi, et al., Optical Sensing Systems for Microfluidic Devices: A Review. Analytica Chimica Acta. 2007;601(2):141-55.
Linder et al., Reagent-loaded cartridges for valveless and automated fluid delivery in microfluidic devices. Anal Chem. Jan. 1, 2005;77(1):64-71.
Llobera et al., Multiple Internal Reflection Poly(dimethylsiloxane) Systems for Optical Sensing. Lab Chip. 2007;7:1560-6.
Lucas et al., An Improved Method for Double-Sided Molding of PDMS. J. Micromech Microeng. 2008;18(7):1-5.
Maselli, et al., Integration of Optical Waveguides and Microfluidic Channels Fabricated by Femtosecond Laser Irradiation. Lasers and Electro-Optics 2007. CLEO 2007. Conference on, May 6-11, 2007, pp. 1-2.
Moorthy et al., Microfluidic Tectonics Platform: A colorimetric, disposable botulinum toxin enzyme-linked immunosorbent assay system. Electrophoresis. Jun. 2004;25(10-11):1705-13.
Obeid et al., Microfabricated device for DNA and RNA amplification by continuous-flow polymerase chain reaction and reverse transcription-polymerase chain reaction with cycle No. selection. Anal Chem. Jan. 15, 2003;75(2):288-95.
Proceedings of uTAS 2004, 8th International Conference on Miniaturized Systems in Chemistry and Life Sciences, Sep. 26-30, Malmo, Sweden, Edited by Thomas Laurell, Johan Nilsson, Klays Jensen, D. Jed Harrison, Jorg P. Kutter, The Royal Society of Chemistry, pp. 1-135 (2004).
Sia et al., An integrated approach to a portable and low-cost immunoassay for resource-poor settings. Angew Chem Int Ed Engl. Jan. 16, 2004;43(4):498-502.
Sia et al., Microfluidic devices fabricated in poly(dimethylsiloxane) for biological studies. Electrophoresis. Nov. 2003;24(21):3563-76.
Song et al., A microfluidic system for controlling reaction networks in time. Angew Chem Int Ed. 2003;42(7):767-772.
Weigl et al., Lab-On-A-Chip for Drug Development. Adv Drug Deliv Rev. Feb. 24, 2003;55(3):349-77.
Yang et al., New Production Method of Convex Microlens Arrays for Integrated Fluorescence Microfluidic Detection Systems. Microsyst Technol.2006;12: 907-12.
Yun et al., Fabrication of Complex Multilevel Microchannels in PDMS by Using Three-Dimensional Photoresist Masters. Lab Chip. 2008;8:245-50.
Becker et al., Sensitive and specific immunodetection of human glandular kallikrein 2 in serum. Clin Chem. Feb. 2000;46(2):198-206.
Benchikh et al., A panel of kallikrein markers can predict outcome of prostate biopsy following clinical work-up: An independent validation study from the European Randomized Study of Prostate Cancer screening, France. BMC Cancer, 10:635 (2010).
Chun et al., Development and external validation of an extended 10-core biopsy nomogram. European Urology, 52:436-445 (2007).
Eriksson et al., Dual-label time-resolved immunofluorometric assay of free and total prostate-specific antigen based on recombinant Fab fragments. Clin Chem. May 2000;46(5):658-66.
Genbank Accession No. 93091201. Feb. 23, 2011.
Gupta et al., A four-kallikrein panel for the prediction of repeat prostate biopsy: Data from the European Randomized Study of Prostate Cancer Screening in Rotterdam, Netherlands. Br. J. Cancer, 103:708-714 (2010).
Hara et al., Total and free prostate-specific antigen indexes in prostate cancer screening: value and limitation for Japanese populations. Asian J. Androl., 8(4):429-434 (2006).
Khan et al., Clinical utility of proPSA and "benign" PSA when percent free PSA is less than 15%. Urology, 64(6):1160-1164 (2004).
Lee et al., A meta-analysis of the performance characteristics of the free prostate-specific antigen test. Urology, 67(4):762-768 (2006).
Lilja et al., Prostate-specific antigen and prostate cancer: prediction, detection and monitoring. Nat. Rev. Cancer, 8(4):268-278 (2008).
Lilja et al., Prostate-specific antigen in serum occurs predominantly in complex with alpha 1-antichymotrypsin. Clin Chem. Sep. 1991;37(9):1618-25.
Lövgren et al., Enzymatic action of human glandular kallikrein 2 (hK2). Substrate specificity and regulation by Zn2+ and extracellular protease inhibitors. Eur J Biochem. Jun. 1999;262(3):781-9.

(56) References Cited

OTHER PUBLICATIONS

Lövgren et al., Production and activation of recombinant hK2 with propeptide mutations resulting in high expression levels. Eur J Biochem. Dec. 1999;266(3):1050-5.

Michielsen et al., Prediction of free PSA, PSA density and PSA density transition zone in the outcome of sextant prostate biopsies in patients with total PSA between 3 and 15 ng/ml. UroOncology, 4(2):71-76 (2004).

Nam et al., Assessing individual risk for prostate cancer. J. Clin. Oncol., 25(24):3582-3588 (2007).

Nam et al., Prospective multi-institutional study evaluating the performance of prostate cancer risk calculators. J. Clin. Oncol., 29(22):2959-2964 (2011).

Nam et al., Variants of the hK2 protein gene (KLK2) are associated with serum hK2 levels and predict the presence of prostate cancer at biopsy. Clin. Cancer Res., 12(21):6452-6458 (2006).

Nurmikko et al., Production and characterization of novel anti-prostate-specific antigen (PSA) monoclonal antibodies that do not detect internally cleaved Lys145-Lys146 inactive PSA. Clin Chem. Oct. 2000;46(10):1610-8.

Parekh et al., External validation of the Prostate Cancer Prevention Trial risk calculator in a screened population. Urology, 68(6):1152-1155 (2006).

Peltola et al., Immunoassay for the discrimination of free prostate-specific antigen (fPSA) forms with internal cleavages at $Lys_{145}$ or $Lys_{146}$ from fPSA without internal cleavages at $Lys_{145}$ or $Lys_{146}$. J Immunol Methods, Jun. 30, 2011;369(1-2):74-80. doi: 10.1016/j.jim.2011.04.006. Epub Apr. 28, 2011.

Peltola et al., Intact and internally cleaved free prostate-specific antigen in patients with prostate cancer with different pathologic stages and grades. Urology, 77(4):1009.e1-1009.e8 (2011).

Piironen et al., Determination and analysis of antigenic epitopes of prostate specific antigen (PSA) and human glandular kallikrein 2 (hK2) using synthetic peptides and computer modeling. Protein Sci. Feb. 1998;7(2):259-69.

Rajakoski et al., Epitope mapping of human prostate specific antigen and glandular kallikrein expressed in insect cells. Prostate Cancer Prostatic Dis. Sep. 1997;1(1):16-20.

Sokoll et al., A prospective, multicenter, National Cancer Institute Early Detection Research Network study of [-2]proPSA: improving prostate cancer detection and correlating with cancer aggressiveness. Cancer Epidemiol. Biomarkers Prev., 19(5):1193-1200 (2010).

Talvitie, Delfia immunoassays: Guide to Converting ELISA Assays to DELFIA. PerkinElmer Life and Analytical Sciences. Dec. 18, 20026:1-16. Retrieved on Jun. 11, 2015 from http://www.perkinelmer.com/cmsresources/images/man_delfia_elisa_conversion.pdf.

Thompson et al., Assessing prostate cancer risk: results from the prostate cancer prevention trial. J. Natl. Cancer Inst., 98:529-534 (2006).

Ulmert et al, Prostate-specific antigen at or before age 50 as a predictor of advance prostate cancer diagnosed up to 25 years later: A case-control study. BMC Medicine, 6(6):1-8 (2008).

Ulmert et al., Reproducibility and accuracy of measurements of free and total prostate-specific antigen in serum vs plasma after long-term storage at -20 degrees C. Clin. Chem., 52(2):235-239 (2006).

Van Vugt et al., Prediction of prostate cancer in unscreened men: external validation of a risk Calculator. Eur. J. Cancer 47(6):903-909 (2011).

Vickers et al., A four-kallikrein panel predicts prostate cancer in men with recent screening: Data from the European Randomized Study of Prostate Cancer Screening, Rotterdam. Clin. Cancer Res., 16(12):3232-3239 (2010).

Vickers et al., A panel of kallikrein marker predicts prostate cancer in a large, population-based cohort followed for 15 years without screening. Cancer Epidemiol. Biomarkers Prey., 20(2):255-261 (2011).

Vickers et al., a panel of kallikrein markers can reduce unnecessary biopsy for prostate cancer: Data from the European Randomized Study of Prostate Cancer Screening in Goteborg, Sweden. BMC Med., 6:19 (2008).

Vickers et al., Decision curve analysis: a novel method for evaluating prediction models. Med Decis Making. Nov.-Dec. 2006;26(6):565-74.

Vickers et al., Impact of recent screening on predicting the outcome of prostate cancer biopsy in men with elevated PSA: Data from the European Randomized Study of Prostate Cancer Screening in Gothenburg, Sweden. Cancer, 116(11):2612-2620 (2010).

Vickers et al., Reducing unnecessary biopsy during prostate cancer screening using a fourkallikrein panel: an independent replication. J. Clin. Oncol., 28(15):2493-2498 (2010).

Wenske et al., Evaluation of molecular forms of prostate-specific in predicting biochemical failure after radical prostatectomy. Int J Cancer. Feb. 1, 2009;124(3):659-63. doi: 10.1002/ijc.23983.

[No Author Listed], Human Prostate-Specific Antigen (PSA) Kit Technical Data Sheet. AlphaLISA Research Reagents. Perkin Elmer. Waltham, MA. 2009. 9 pages.

Nurmikko et al., Discrimination of prostate cancer from benign disease by plasma measurement of intact, free prostate-specific antigen lacking an internal cleavage site at Lys145-Lys146. Clin Chem. Aug. 2001;47(8):1415-23.

U.S. Appl. No. 15/197,107, filed Jun. 29, 2016, Linder et al.
U.S. Appl. No. 15/197,148, filed Jun. 29, 2016.
U.S. Appl. No. 15/197,172, filed Jun. 29, 2016

* cited by examiner

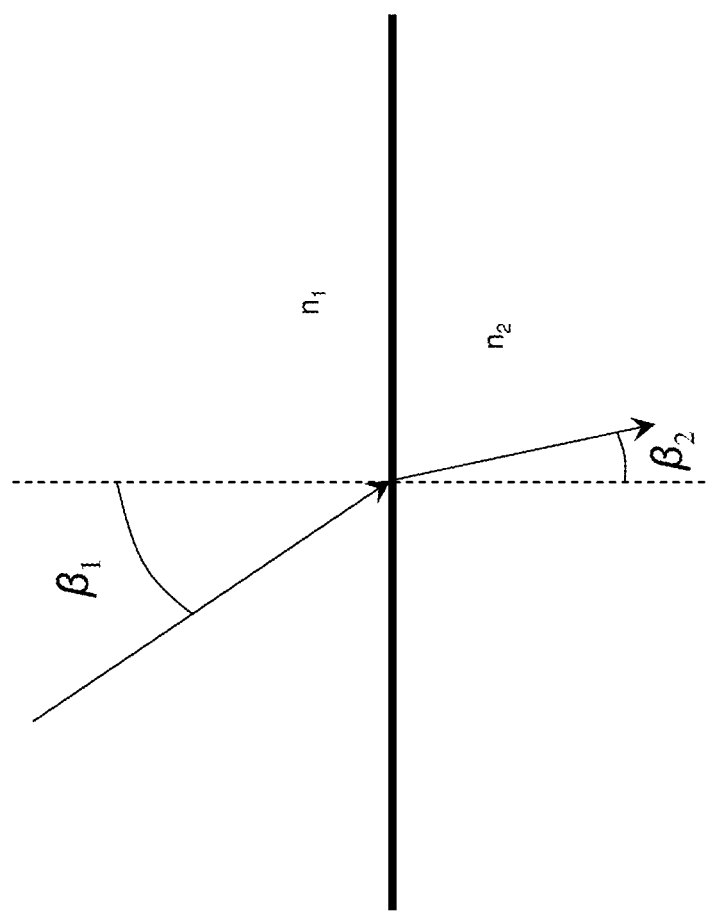

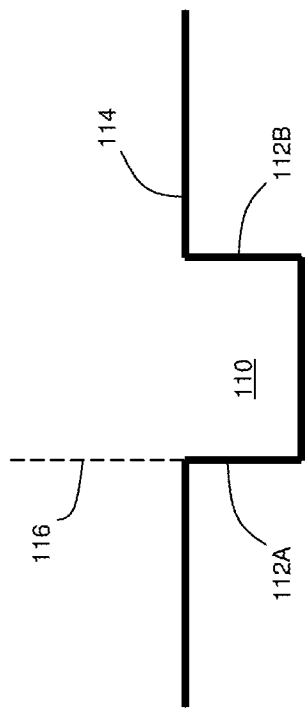
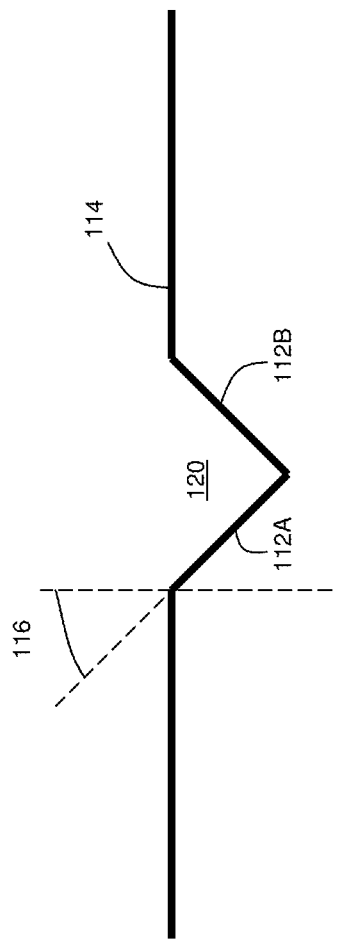

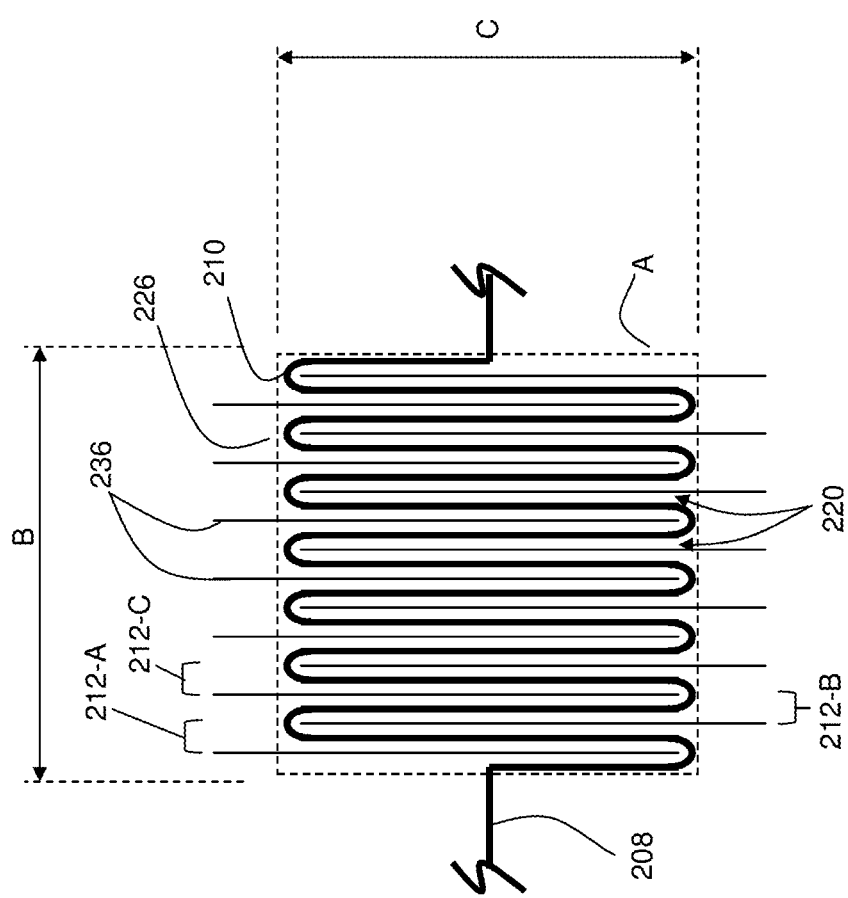

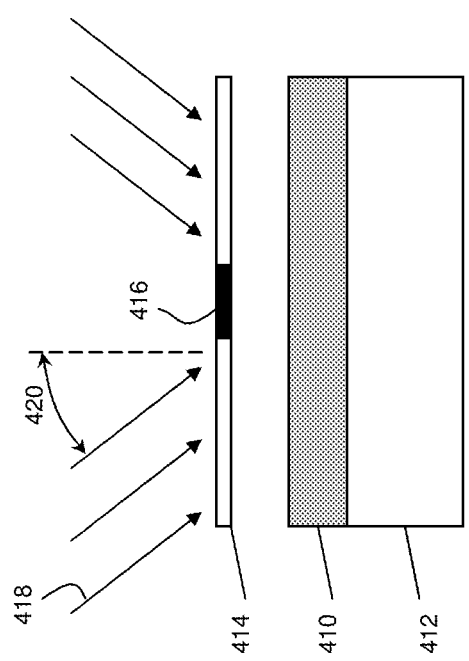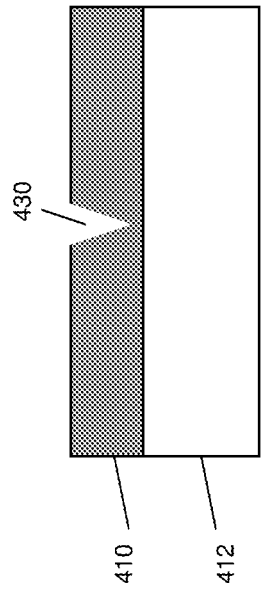

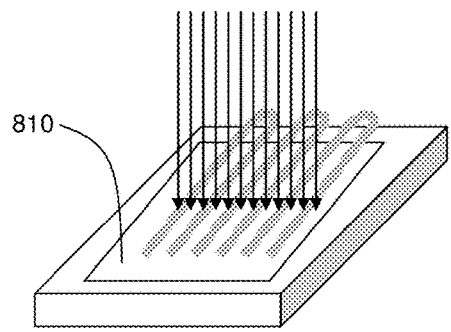 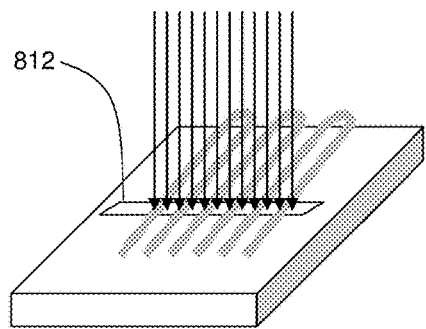
FIG. 8A  FIG. 8B
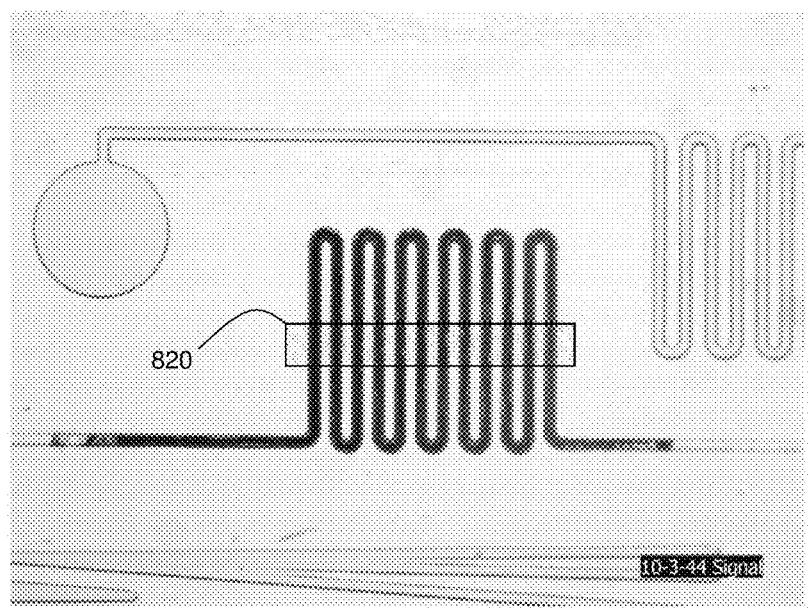
FIG. 8C

FLUIDIC SYSTEMS AND METHODS FOR ANALYSES

RELATED APPLICATIONS

This is a continuation application of U.S. patent application Ser. No. 14/316,069, filed Jun. 26, 2014, and entitled "Structures for Controlling Light Interaction with Microfluidic Devices," which is a continuation application of U.S. patent application Ser. No. 13/898,028, filed May 20, 2013, and entitled "Structures for Controlling Light Interaction with Microfluidic Devices," which is a divisional application of U.S. patent application Ser. No. 13/490,055, filed Jun. 6, 2012, and issued as U.S. Pat. No. 8,480,975 on Jul. 9, 2013, and entitled "Structures for Controlling Light Interaction with Microfluidic Devices," which is a continuation of U.S. patent application Ser. No. 12/698,451, filed Feb. 2, 2010 and issued as U.S. Pat. No. 8,221,700 on Jul. 17, 2012, and entitled "Structures for Controlling Light Interaction with Microfluidic Devices," which claims priority under 35 U.S.C. §119(e) to U.S. Provisional Patent Application No. 61/149,253, filed Feb. 2, 2009, and entitled "Structures for Controlling Light Interaction with Microfluidic Devices," each of which is incorporated herein by reference in its entirety for all purposes.

FIELD OF INVENTION

The present invention relates generally to microfluidic systems, and more specifically, to systems and methods for controlling light interaction with microfluidic devices.

BACKGROUND

Optical analysis of fluids plays an important role in fields such as chemistry, microbiology and biochemistry. These fluids may include liquids or gases and may provide reagents, solvents, reactants, or rinses to chemical or biological processes. While various microfluidic methods and devices, such as microfluidic assays, can provide inexpensive, sensitive and accurate analytical platforms, carrying out accurate optical measurements (e.g., absorbance or transmission) on a microfluidic system can be challenging. Optical measurements of microchannels may require, for example, time-consuming alignment procedures. In addition, optical noise produced by light incident upon areas outside the channels may degrade the quality of the detected signal through the channels. Accordingly, advances in the field that could reduce costs, simplify use, and/or improve optical detection in microfluidic systems would be beneficial.

SUMMARY OF THE INVENTION

Systems and methods for controlling light interaction with microfluidic devices are provided. The subject matter of the present invention involves, in some cases, interrelated products, alternative solutions to a particular problem, and/or a plurality of different uses of one or more systems and/or articles.

In one set of embodiments, a series of fluidic devices are provided. In one particular embodiment, a fluidic device comprises an article including first and second opposing sides and first and second microfluidic channel segments, each integral to the first side of the article. The fluidic device also includes an intervening portion positioned substantially between the first and second microfluidic channel segments, and a first optical element integral to the second side of the article and positioned substantially between the first and second channel segments, and opposite the intervening portion. The first optical element is adapted and arranged such that when a portion of the article is exposed to light at a first intensity, the first optical element redirects at least a portion of the light away from the intervening portion, such that the intervening portion is not exposed to the light or is exposed to the light at a second intensity lower than an intensity of the light at the intervening portion absent the first optical element.

In another embodiment, a fluidic device comprises an article comprising first and second sides, a first microfluidic channel segment integral to the first side of the article, and first and second optical elements, each integral to the second side of the article, wherein the first microfluidic channel segment is positioned substantially between the first and second optical elements. A cover is positioned over the first microfluidic channel segment so as to substantially enclose the first microfluidic channel segment. Furthermore, an intervening surface portion at the second side of the article is positioned substantially between the first and second optical elements, the intervening surface portion being substantially parallel to a surface portion of the cover that substantially encloses the first microfluidic channel segment.

In another embodiment, a fluidic device comprises an article comprising first and second sides, and first and second microfluidic channel segments, each integral to the first side of the article. The fluidic device also includes a first substantially triangular optical element integral to the second side of the article and positioned substantially between the first and second channel segments.

In some instances, the first and/or second microfluidic channel segments described above and herein are sections of a microfluidic channel comprising a meandering configuration including multiple turns, each turn of the meandering channel being a different channel segment.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1E include schematic diagrams of a device including optical elements that can be used to control light interaction on or within the device, according to one set of embodiments;

FIGS. 3A-3C include, according to one set of embodiments, schematic diagrams of channel configurations in certain devices;

FIGS. 4A-4B include cross-sectional diagrams illustrating a fabrication process, according to one set of embodiments;

FIGS. 8A-8C include schematic diagrams illustrating various sensor layouts, according to one set of embodiments;

DETAILED DESCRIPTION

Figure 1A:
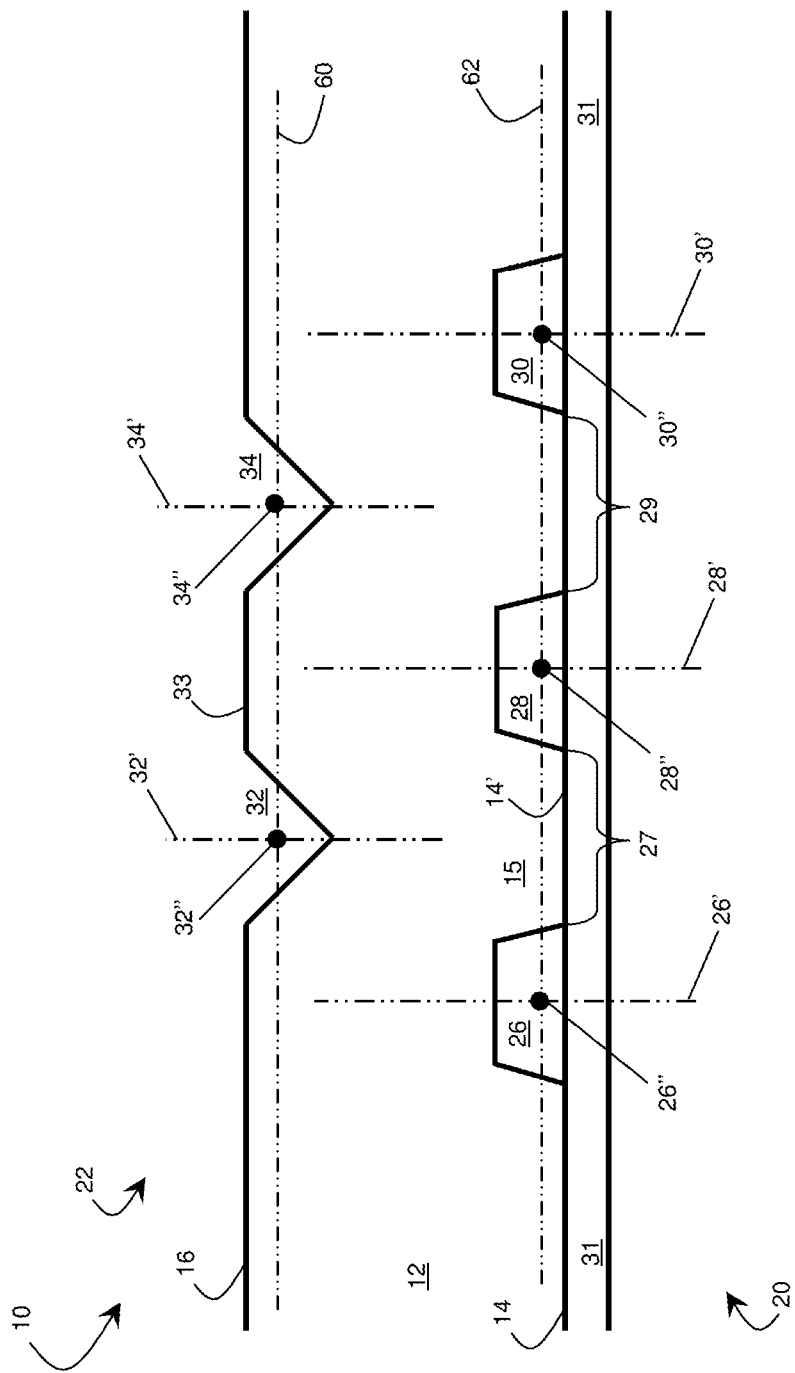

Systems and methods for improved measurement of absorbance/transmission through fluidic systems are described. Specifically, in one set of embodiments, optical elements are fabricated on one side of a transparent fluidic device opposite a series of fluidic channels. The optical elements may guide incident light passing through the device such that most of the light is dispersed away from specific areas of the device, such as intervening portions between the fluidic channels. By decreasing the amount of light incident upon these intervening portions, the amount of noise in the detection signal can be decreased when using certain optical detection systems. In some embodiments, the optical elements comprise triangular grooves formed on or in a surface of the device. The draft angle of the triangular grooves may be chosen such that incident light normal to the surface of the device is redirected at an angle dependent upon the indices of refraction of the external medium (e.g., air) and the device material.

Advantageously, certain optical elements described herein may be fabricated along with the fluidic channels of the device in one step, thereby reducing the costs of fabrication. Furthermore, in some cases the optical elements do not require alignment with a detector and, therefore, facilitate assembly and/or use by an end user. Other advantages are described in more detail below.

Additional techniques may be employed to reduce the amount of stray light transmitted through the fluidic device. For example, in some instances, the widths of the intervening portions between the channel segments may be reduced. Also, the light source may be arranged such that light is emitted only over portions of the device that lie above the channel segments. Both of these techniques may reduce the amount of light transmitted through the intervening portions, thus improving the quality of the optical image. In some embodiments, the fluidic device may include a detector array arranged such that the areas of the array under the channel segments are sensitive to light, while the other areas of the array are not.

The systems and methods described herein may find application in a variety of fields. In some cases, the systems and methods can be used to improve the optical performance of any microfluidic system such as, for example, microfluidic point-of-care diagnostic platforms, microfluidic laboratory chemical analysis systems, optical monitoring systems in cell cultures or bio-reactors, among others. Optical measurements in microfluidic systems may be used to monitor any suitable chemical and/or biological reaction as it takes place, diagnostic or otherwise. As a specific example, an optical measurement step can be used during DNA synthesis to verify the yield of each base addition (e.g., optical trityl monitoring) and during some forms of PCR amplification to monitor the process.

Previous systems, such as those described in International Patent Publication No. WO2006/113727 (International Patent Application Serial No. PCT/US2006/014583), filed Apr. 19, 2006 and entitled "Fluidic Structures Including Meandering and Wide Channels," have made use of a meandering microchannel to image a two-dimensional space. For example, a microfluidic channel may be in the form of a tight "S" shape having multiple channel segments, forming an area of about 2 mm, e.g., a "measurement area" including both channel and non-channel regions. In certain embodiments, this measurement area does not require fine alignment for optical measurements (unlike a single straight channel) and forms a measurement area which can be easily interrogated optically. For instance, a detector may be positioned over all or a portion of the measurement area made up of channel and non-channel regions. One limitation of the use of meandering structures in the context of transmission measurement, though, is that some of the light shining through these measurement areas will pass through the intervening portions between the microfluidic channel segments (that is, the non-channel regions). This light may reach the optical detector without reflecting changes in the optical density of the contents of the microchannel. This "stray light" can reduce the overall performance of the optical detection. This effect may be particularly problematic when making measurements of channels with high levels of optical density. A large amount of stray light on the detector may wash out any changes in small amounts of light passing through the microchannels.

The inventors have discovered within the context of the invention that the amount of light that passes through an intervening portion between microfluidic channels or channel segments may be reduced or substantially eliminated by fabricating, in the device, at least one optical element. The optical element may redirect at least a portion of the light away from the intervening portion, such that the intervening portion is not exposed to the light or is exposed to the light at a second intensity lower than an intensity of light to which the intervening portion would be exposed in the absence of the optical element. The incorporation of optical elements into microfluidic channel systems enhances the performance of the detection system, allowing the use of simplified optics without compromising the quality of the optical measurements.

Furthermore, the systems and methods described herein may be used to improve alignment in micro-scale optical detection systems. Certain methods for optical detection/measurements in microsystems are challenging in that they require accurate alignment of the optics with micro-scale features (e.g., microchannels). Such alignment can be performed manually (e.g., with a microscope and micrometric stage) in a labor-intensive fashion, or in an automated manner (e.g., using complex robotic positioning systems).

These techniques, however, often require a skilled and attentive operator or expensive, delicate automation, making them suboptimal for certain applications. The ability of the optical elements to redirect light away from one or more intervening portions between microfluidic channel segments may eliminate or reduce the need for such complicated alignment procedures.

Additionally, the positioning of a detector over a measurement area without the need for precision is an advantage, since external (and possibly, expensive) equipment such as microscopes, lenses, and alignment stages may not be required. Instead, alignment can be performed by eye, or by low-cost methods that may not require an alignment step by the user. For example, in one embodiment, a fluidic device comprising one or more optical elements and a measurement area including both channel and non-channel regions can be placed in a simple holder (i.e., in a cavity having the same shape as the fluidic device), and the measurement area can be automatically aligned with a beam of light of the detector.

It should be noted that the systems and methods described herein may be used for guiding light in any suitable system utilizing microfabricated structures, and are not limited to microfluidic systems and/or the specific channel configurations described herein.

Additional advantages of devices including optical elements constructed to redirect light are described in more detail below.

The articles, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, filed May 1, 2008 and entitled "Fluidic Connectors and Microfluidic Systems"; U.S. patent application Ser. No. 12/196,392, filed Aug. 22, 2008, entitled "Liquid containment for integrated assays"; U.S. patent application Ser. No. 12/428,372, filed Apr. 22, 2009, entitled "Flow Control in Microfluidic Systems"; U.S. Patent Apl. Ser. No. 61/263,981, filed Nov. 24, 2009, entitled "Fluid Mixing and Delivery in Microfluidic Systems"; and U.S. patent application Ser. No. 12/640,420 filed on Dec. 17, 2009 and entitled, "Improved Reagent Storage in Microfluidic Systems and Related Articles and Methods," each of which is incorporated herein by reference in its entirety for all purposes. In addition, U.S. Provisional Patent Application Ser. No. 61/149,253, filed Feb. 2, 2009, entitled "Structures for Controlling Light Interaction with Microfluidic Devices," is incorporated herein by reference in its entirety for all purposes.

Examples of fluidic devices and methods associated therewith are now provided.

Figure 1B:
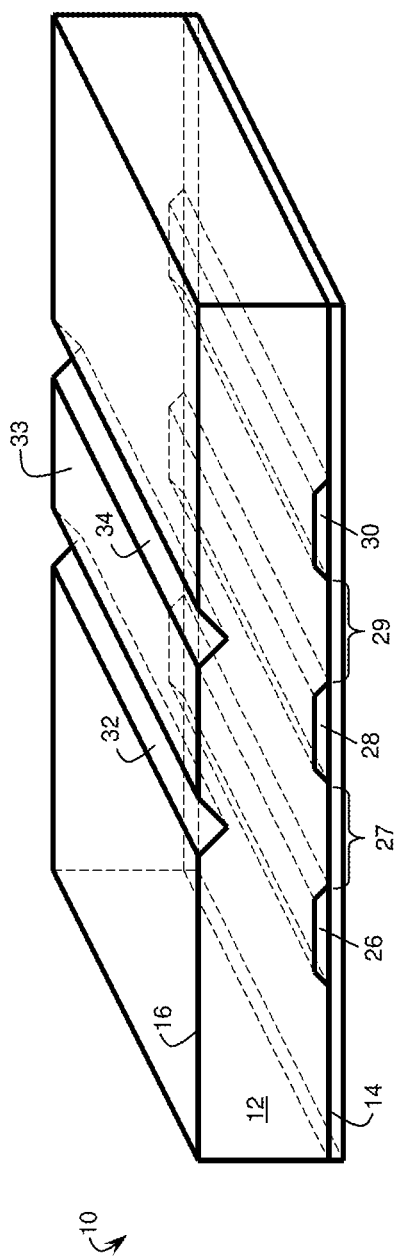

FIGS. 1A-1E show various portions of a fluidic device including optical elements that can be used to control light interaction on or within the device. FIG. 1A shows a cross section and FIG. 1B shows a perspective view of a fluidic device 10 which includes an article 12 having a first surface 14 and a second surface 16, as well as a first side 20 and a second side 22.

As used herein, "first and second sides" of an article generally refers to the relative orientation of two portions of the article. First and second sides may refer to first and second surfaces of the article, or to a portion of the article that does not encompass a surface, e.g., a portion of the article that is embedded within the bulk of the article. For example, first and second microfluidic channel segments that are said to be integral to the first side of the article may be integral to a surface at the first side of the article or embedded within the article at the first side. FIG. 1A also shows the first side opposing the second side. Two sides are said to be "opposing" when they are substantially parallel to each other and separated by a distance.

Figure 1C:
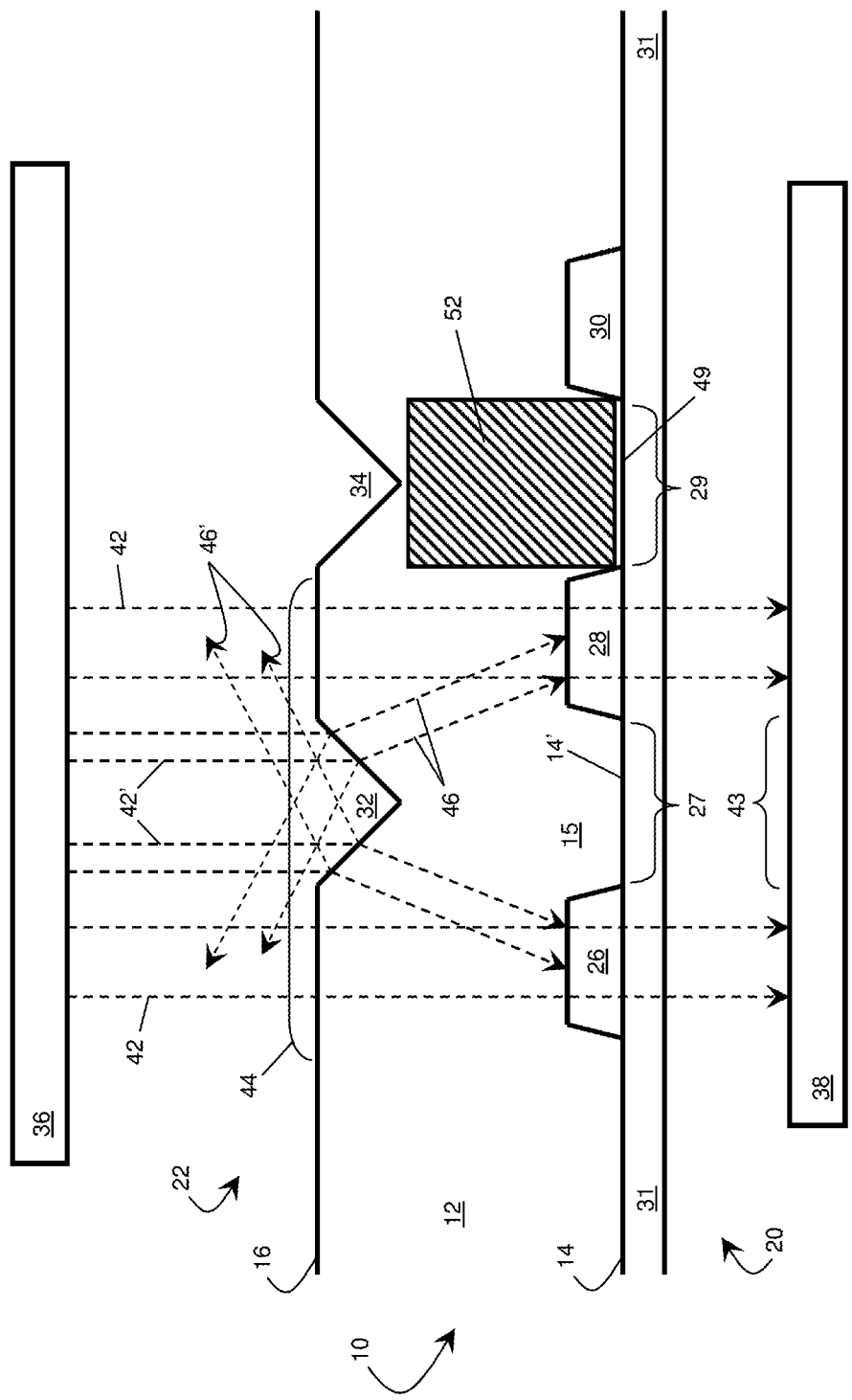
Figure 1D:
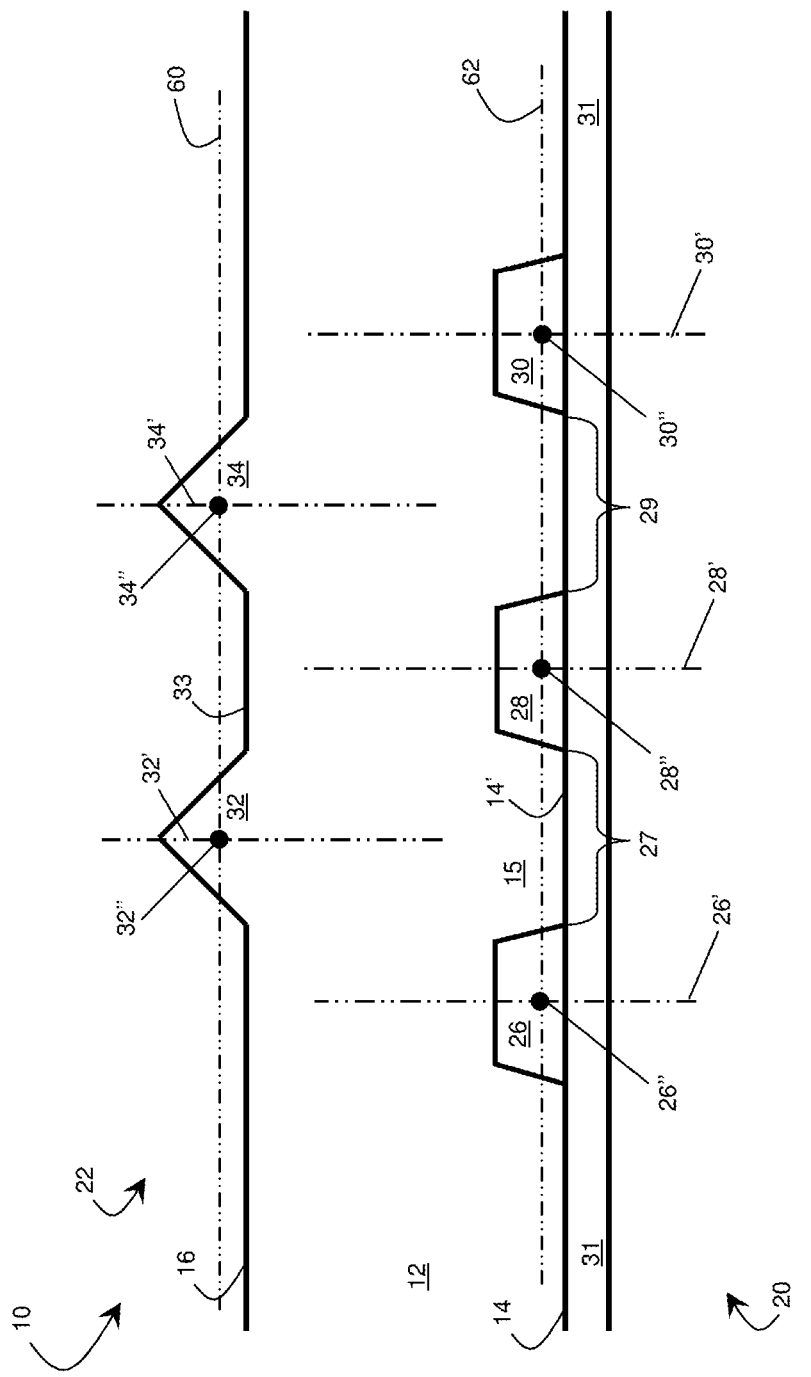

As shown illustratively in FIGS. 1A and 1C, first side 20 includes a plurality of channel segments (first 26, second 28, and third 30) formed therein. A channel segment refers to a portion of a fluidic channel that spans an entire cross-section of the channel and has a length substantially parallel to fluid flow. A channel segment may have any suitable length, e.g., at least 1 mm, at least 5 mm, at least 1 cm, or at least 5 cm in certain embodiments. While three channel segments are shown in FIG. 1A, systems and methods described herein may comprise any suitable number of channel segments and may be configured in any suitable arrangement. For instance, channel segments of a device may be a part of the same fluidic channel, or may be part of separate fluidic channels that are not in fluid communication with one another.

In some embodiments, channel segments refer to a series of repetitive units of one or more channels; for example, each channel of an array of channels may be a channel segment. In another example, a channel includes a plurality of reaction areas positioned in series, and each channel portion associated with a distinct reaction area is a channel segment. In certain cases, channel segments are sections of a fluidic channel having a meandering configuration, each "turn" of the meandering channel being a different channel segment. As used herein, a "meandering channel" (i.e., a channel having a meandering region) includes at least a first segment that has a flow path in a first direction and a second segment that has a flow path in a second direction substantially opposite (e.g., greater than 135 degrees from) the first direction. Often, a meandering channel will include more than two alternating channel segments that extend in opposite directions. Examples of meandering channel regions are provided below.

In some embodiments, the two or more channel segments of a device are spaced apart from each other by intervening portions, i.e., non-channel portions. For instance, first side 20 includes intervening portions 27 and 29. An intervening portion may include portions of a surface of an article (e.g., surface portion 14' of FIG. 1A) and/or a portion of the article that does not encompass a surface (e.g., portions 15 of FIG. 1A). In some embodiments, an intervening portion has one or more dimensions (e.g., a width, height, and/or length) of at least 0.5 mm, at least 1 mm, at least 5 mm, at least 1 cm, or at least 5 cm in certain embodiments. A dimension of an intervention portion may, for example, define the distance between two channel segments.

The fluidic device illustrated in FIGS. 1A and 1C also includes a cover 31 positioned over the plurality of channel segments. The cover may be positioned over the channel segments so as to substantially enclose the channel segments. In some instances, the cover may comprise a tape (e.g., flexible tape), glass (e.g., a cover slide), rigid plastic, or any other suitable material as described in more detail below.

In the set of embodiments illustrated in FIGS. 1A and 1C, second side 22 includes a plurality of optical elements (first 32 and second 34) formed therein. As used herein, the term "optical element" is used to refer to any feature formed or positioned on or in an article or device that changes the direction (e.g., via refraction or reflection), focus, polarization, and/or other property of incident electromagnetic radiation relative to the light incident upon the article or device in the absence of the element. For example, an optical element may comprise a lens (e.g., concave or convex), mirror, grating, groove, or other feature formed or positioned in or on an article. An article itself absent a unique feature, however, would not constitute an optical element, even though one or more properties of incident light may change upon interaction with the article.

FIGS. 1A and 1C also show an intervening surface portion 33 between the first and second optical elements. As shown in FIG. 1A, the intervening surface portion may be substantially parallel to the surface portion of the cover that substantially encloses the microfluidic channel segments. While two optical elements are shown in FIGS. 1A and 1C, the articles described herein may comprise any suitable number of optical elements and any suitable number of intervening surface portions between the optical elements. Furthermore, some articles do not include intervening surface portions between the optical elements, e.g., a series of optical elements may be configured to form alternating ridges and grooves in a corrugated fashion.

The optical elements described herein may be, in some cases, substantially transparent (e.g., to visible light, infrared radiation, etc.). In other embodiments, optical elements may comprise a substantially opaque material. In some cases, optical elements may comprise one or more reflective surfaces. For example, an optical element may comprise a channel, the walls of which are coated with a reflective material such as a metal (e.g., Ni, Ag, Au, Pt) or a semiconductor (e.g., Si, glass).

An optical element may comprise a groove, which may be open or substantially enclosed. As shown in the embodiment illustrated in FIGS. 1A and 1C, optical elements 32 and 34 are in the form of grooves that are substantially triangular; however, other shapes are also possible. For instance, in other embodiments, the cross-section of an optical element may be of any suitable shape such as a hemisphere, square, rectangle, trapezoid, etc. Some optical elements have a semi-spherical or semi-ovular shape. The shape and/or angle of the groove may be selected such that incident light normal to the surface of the device is redirected away from the area directly below the groove. This may enhance the probability that little or no light is incident upon unwanted areas around the channels (e.g., intervening portions 27 and 29), reducing the amount of noise in the detection signal. Accordingly, an optical element may have any suitable size, configuration, and/or shape to achieve improvements in signal to noise, as described in more detail below.

In some cases, an optical element may be a feature that protrudes from a surface of an article. For example, FIG. 1D includes triangular optical elements 32 and 34 formed in the shape of a prism. It should be understood that "triangular" optical elements include any elements that are triangular in cross-section, whether formed in a substrate (e.g., as in FIG. 1A) or on a substrate (e.g., as in FIG. 1D). Other shapes that may be formed include, for example, half-cylinders, rectangular prisms, etc.

An optical element may comprise, in some cases, one or more fluids (e.g., a dye). For example, in one set of embodiments, the optical element is formed as a channel (e.g., by placing a cover over surface 16 of the article) and the channel is filled with a light-absorbing fluid such as an opaque dye. Dyes of any suitable concentration may be used. In some embodiments, the concentration of the dye may be at least about 0.1 grams, at least about 0.5 grams, at least about 1 gram, at least about 5 grams, at least about 10 grams, at least about 50 grams, or at least about 100 grams of dye material per mL of solvent (e.g., water).

FIG. 1C shows a schematic diagram of an optical device during operation, according to one set of embodiments. During operation, fluidic device 10 is positioned between a light source 36 and an optical detector 38 such that first side 20 (comprising one or more channel segments) faces the detector and second side 22 (comprising one or more optical elements) faces light source 36 and is exposed to light 42. The detector may be associated with one or more fluidic channel segments in the fluidic device, e.g., to determine light transmission through one or more of the channel segments. In one set of embodiments, when a portion of the article is exposed to light at a first intensity, the optical elements redirect at least a portion of the light away from the intervening portions. For example, one or more optical elements may be adapted and arranged so as to redirect at least a portion of the light away from a surface portion of the first side, the surface portion being adjacent to at least one channel segment. In FIG. 1C, optical element 32 is adapted and arranged to redirect light away from intervening portion 27, which includes surface portion 14'. Similarly, optical element 34 is adapted and arranged to redirect light away from intervening portion 29, which includes surface portion 49. Redirecting light may include, for instance, reflecting the light (e.g., away from the article), refracting the light (e.g., through the article in a direction away from the intervening portion), or both.

One or more optical elements may be constructed and arranged to redirect at least about 10%, at least about 25%, at least about 50%, at least about 75%, or at least about 90% of incident light away from an intervening portion. As light is redirected, the intervening portions are not exposed to the light or are exposed to the light at a second intensity lower than an intensity of the light at the intervening portion absent the optical elements. For example, in some cases, at least one optical element is adapted and arranged such that the intervening portions are exposed to the light at a second intensity at least about 50% lower, at least about 75% lower, or at least about 90% lower than an intensity of the light at the intervening portion absent the optical elements.

In some embodiments, one or more optical elements are adapted and arranged so as to redirect at least a portion of the light away from the center plane (e.g., 32' and 34' in FIG. 1A) of the optical element, such that the underlying portion of the device directly below the optical element is not exposed to light or is exposed to light at a second intensity lower (e.g., about 25% lower) than the intensity to which the underlying portion would be exposed were the optical element absent. As used herein, a region is "directly below" an object when it lies on the side of an object opposite that which is exposed to light from the source. The region directly below an object may span the width of the object and the depth of the article perpendicular to the outermost surface on either the first or second side of the object. For example, in FIG. 1C, region 52 lies directly below optical element 34.

An example of the use of optical elements to redirect light is shown in FIG. 1C. As illustrated in FIG. 1C, portion 44 of article 12 is exposed to light 42 from the light source. In some cases, the light source and device are oriented such that the angle of incidence of the light on surface 16 is between about 85° and about 95°, or at substantially 90°. At surface 16, light that is incident on areas absent the optical elements is transmitted into the bulk of the device without a substantial change in direction, as indicated by arrows 42. Light incident upon optical element 32, however, interacts at an angle substantially different than 90°. Optical element 32 redirects at least a portion of the light away from intervening portion 27, e.g., by reflection, refraction, and/or both. Arrows 46' represent light that is reflected away from the optical element, while arrows 46 illustrate light that is refracted through the article, but away from intervening portions between the fluidic channels. Thus, intervening portion 27 is not exposed to the light, or is exposed to the light at an intensity less than it would have been in the absence of optical element 32. Furthermore, although not shown in this figure, light may be absorbed by the article or redirected at other angles, thereby reducing the amount of light detected by the detector at intervening portion 27. Optical element 34 functions in a similar manner, in this case redirecting light away from intervening portion 29 and generally away from region 52 directly below the optical element.

In some cases, one or more optical elements are adapted and arranged to redirect at least a portion of the incident light into one or more fluidic channels on the opposite side of the article. For example, as shown in FIG. 1C, a portion of the light incident upon optical element 32 is refracted through the article and redirected into fluidic channels 26 and 28. Advantageously, this can increase the amount of light used to interrogate a sample in fluidic channels 26 and 28.

It should be understood that while much of the description and figures herein describe the positioning of optical elements at a side of an article opposite the channels, in some cases the optical elements may positioned at the same side as the channels. For instance, optical elements 32 and 34 of FIG. 1A-1D may be formed in surface 14 and may optionally include a reflective surface so as to redirect light 42' away from portion 43 of the detector. In other cases, an article may include a combination of optical elements formed in or on both surfaces of the article. The geometry of the device and configuration of features may be chosen, in some cases, such that any light passing through the bulk of the article from a first side is redirected toward the channels on the opposite side of the article. The design of a system with optical elements may be undertaken with the goal of both reflecting light and re-directing light away from the intervening portions between channels. Without wishing to be bound by theory, the design of a fluidic device may take into account the following:

The trajectory of refracted light is determined by Snell's Law:

$$n_1 \sin(\beta_1) = n_2 \sin(\beta_2) \quad [1]$$

where $n_1$ and $n_2$ are the indices of refraction of the medium in which the light originates and is transmitted, respectively, $\beta_1$ is the angle between the angle of incidence and the normal at the interface, and $\beta_2$ is the angle of refraction, as outlined in FIG. 1E.

Design features that may be varied to increase the amount of light redirected away from the intervening portions include, for example, the width of the channel (W), the pitch of the optical elements (P1), the pitch of the channels (P2), the depth of the channel (D), the width of the optical elements (V), the draft angle of the optical elements ($\alpha$), the thickness of the microfluidic substrate (T), the index of refraction of microfluidic substrate ($n_2$), the index of refraction of external medium ($n_1$), and the incident angle of light on the substrate (assume perpendicular to substrate).

Figure 2A:
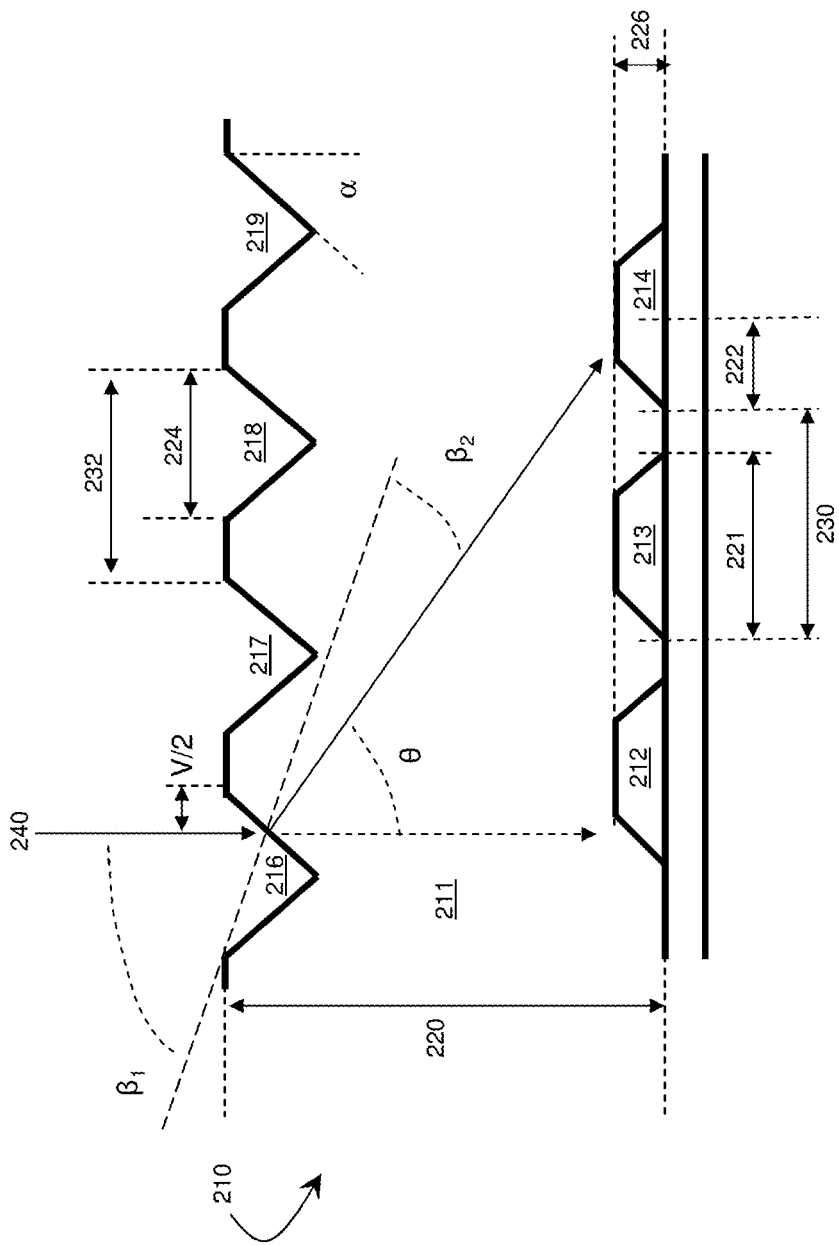
FIGS. 2A-2B include schematic cross-sectional diagrams of devices showing light interactions in the devices, according to one set of embodiments.

For example, FIG. 2A includes device 210 comprising substrate 211 in which channels 212, 213, and 214 and optical elements 216, 217, 218 and 219 are formed. The thickness of the substrate is illustrated by dimension 220 in FIG. 2A. The width of a channel is measured as the widest cross-sectional dimension of the channel substantially parallel to the surface in which it is formed. For example, the width of channel 213 is indicated by dimension 221 in FIG. 2A. The half-width of channel 214 is indicated by dimension 222. Similarly, the width of an optical element is also measured as the widest cross-sectional dimension of the element substantially parallel to the surface in or on which it is formed. For example, the width of optical element 218 is indicated by dimension 224 in FIG. 2A. The depths of the channels, as indicated by dimension 226 in FIG. 2A, are measured perpendicular to the surface in which they are formed.

The pitch of two channels is measured as the distance between a first point on a first channel and a second point on a second channel, wherein the first and second points are located in similar positions within their respective channels. In other words, the pitch is equal to the width of a channel plus the gap between that channel and the adjacent channel. For example, in FIG. 2A, the pitch of channels 213 and 214 may be measured as the distance between similar edges of the channels, as indicated by dimension 230. In some embodiments, the pitches of all adjacent channels are substantially constant, as indicated in FIG. 2A; however, in other cases the pitches between channels may vary. The pitch of two optical elements is measured in a similar manner as shown, for example, by dimension 232 in FIG. 2A. In some embodiments, the pitches of all adjacent optical elements may be substantially constant, or may vary, e.g., depending the particular light interaction desired.

To minimize stray light, improved results are obtained in some embodiments when the pitch (P1) of the optical elements matches the pitch of the channels (P2). The width of the optical elements (V) may be chosen such that the area between the optical elements (P-V) is less than the width of the channel (W). As (P-V) decreases relative to W, the percentage of incident light that is redirected by the optical elements increases. To increase the amount of light redirected away from the intervening portions by the optical elements, the thickness of the system may be set so that light refracted by the optical elements is directed onto the channels. Since there may be multiple channels, there may be multiple preferred thicknesses for the system.

One may create a model to calculate preferred thicknesses by imagining an incident light ray (e.g., perpendicular to the article) striking the article halfway between the bottom and the edge of the optical element (see, for example, light ray 240 in FIG. 2A). The thickness of the article may be selected such that this light reaches the center of a channel. To determine this thickness, one may begin by calculating the angle of the refracted light to the vertical within the substrate ($\beta$). This angle is a function of the angle of incidence, the draft angle of the optical element, and the angle of refraction. Examining the geometry, one can see:

$$\beta_1 = 90 \text{ deg.} - \alpha \quad [2]$$

$$\theta = 90 \text{ deg.} - \alpha - \beta_2 = \beta_1 - \beta_2 \quad [3]$$

Using Snell's Law (Equation 1), the angle of refraction ($\beta_2$) can be calculated as:

$$\beta_2 = \sin^{-1}\left(\frac{n_1}{n_2}\sin\beta_1\right) \qquad [4]$$

Therefore:

$$\theta = 90\deg.-\alpha - \sin^{-1}\left(\frac{n_1}{n_2}\sin(90\deg.-\alpha)\right) \qquad [5]$$

If one were to assume a draft angle ($\alpha$) of 35.3°, an article refractive index ($n_2$) of 1.57 (e.g., polystyrene), and a refractive index of air ($n_1$) of roughly 1.0, the internal angle of refraction would be 23.4°.

Following this ray of from the center of the side of the optical element to the center of a channel, this angle can be used to calculate an intermediate measure of thickness (t):

$$\tan\theta = \frac{x}{t} \qquad [6]$$

Figure 2B:
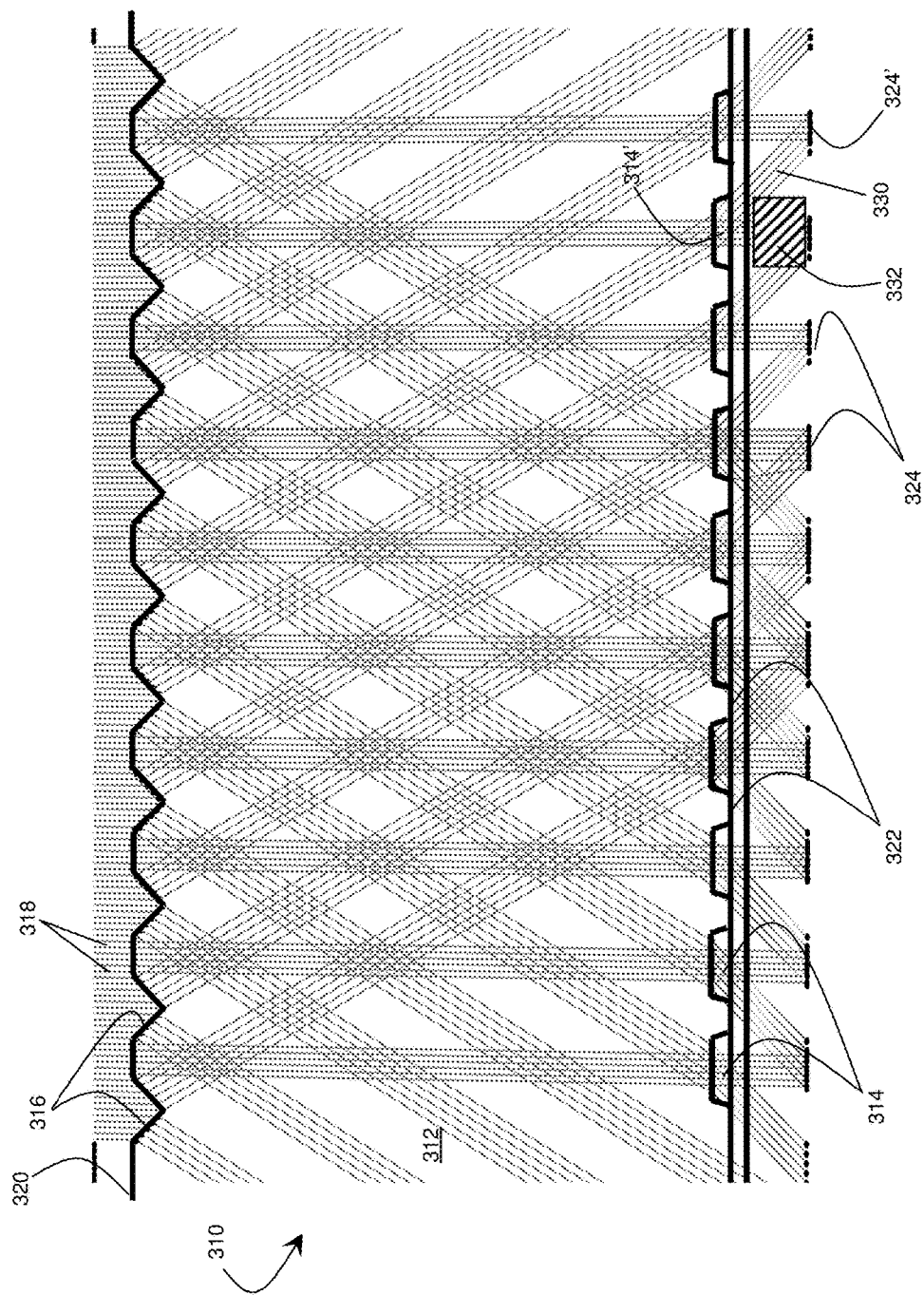

The distance (x) from the point below the incident light and the center of a the closest channel is half the pitch minus the distance between the bottom of the optical element and the edge (V/4). The center of any additional channel is a multiple of the pitch. Note that in FIG. 2A, the thickness was chosen to direct the refracted light onto a channel two channels away (n=2) from the closest channel below the incident light. In FIG. 2B, n=3.

$$x = \left(\frac{P}{2} - \frac{V}{4}\right) + nP \qquad [7]$$

This yields:

$$t = \frac{\left(\frac{P}{2} - \frac{V}{4}\right) + nP}{\tan\theta} \qquad [8]$$

The total thickness of the substrate also includes the depth of the channels and half the depth of the triangular optical elements. Thus, a preferred thickness for a device including triangular optical elements and multiple channel segments can be calculated as:

$$T = t + D + \frac{(V/2)}{\tan\alpha} \qquad [9]$$

Example 2 includes a description of experiments performed using a device designed in this manner.

FIG. 2B includes a ray trace image generated by Mathematica (Lenslab plug-in) of a proposed design of a system including optical elements positioned above microfluidic channels. In FIG. 2B, device 310 comprises article 312 in which channels 314 and optical elements 316 are formed. Light rays 318 are directed toward surface 320 of the article, where a portion of the light is refracted through the article. The device is constructed and arranged such that the light is directed away from intervening portions 322, and toward channels 314 and ultimately detector components 324. Note that in some cases, light that is incident upon a channel does not necessarily interact with the detector at a position directly below the channel. For example, light rays 330 interact with channel 314' and detector component 324', which is not directly below (indicated by region 332) channel 314'.

It should be understood that while triangular optical elements are shown in FIGS. 1-2, a similar analysis can be performed with devices having optical elements of other shapes and configurations.

Light scattering or stray light may be reduced by fabricating the walls of these optical elements to be very smooth. In some embodiments, the root mean square (RMS) surface roughness may be, for example, less than about 1 µm. In other embodiments, the RMS surface roughness may be less than about 0.8 µm, less than about 0.5 µm, less than about 0.3 µm, or less than about 0.1 µm. RMS surface roughness is a term known to those skilled in the art, and may be expressed as:

$$\sigma_h = [\langle(z-z_m)^2\rangle]^{1/2} = \left[\frac{1}{A}\int_A (z-z_m)^{1/2} dA\right]^{1/2}$$

where A is the surface to be examined, and $|z-z_m|$ is the local height deviation from the mean. Substantial roughness on the surface of an optical element may result in unwanted scattering or redirection of light at an undesired angle.

As described herein, optical elements may have various shapes, sizes and configurations. For example, in one set of embodiments, the largest cross-sectional dimension of an optical element is at least about 300 microns, 500 microns, 700 microns, 1 mm, 1.5 mm, 2 mm, or greater (typically, less than 1 cm). In some embodiments, the largest cross-sectional dimension of an optical element is its width. For instance, as shown in FIG. 2A, the largest cross-sectional dimension of optical element 218 is its width 224.

In some cases, e.g., as illustrated in FIG. 2A, at least one optical element (e.g., optical element 218) is positioned between first and second channel segments (e.g., segments 213 and 214, respectively), and the optical element has a largest cross-sectional dimension (e.g., width 224) greater than or equal to the width of an intervening portion positioned substantially between the first and second channel segments, but less than the combination of the widths of the two channel segments and the width of the intervening portion.

Optical elements may, in some cases, span at least about 50%, at least about 60%, at least about 70%, at least about 80%, or at least about 90% of the length of one or more channel segments on or in the article. For example, in FIG. 1B, optical elements 32 and 34 span the entire length of channel segments 26, 28, and 30.

In some fluidic devices described herein, one or more optical elements and/or channels have a non-zero draft angle. As known to those of ordinary skill in the art, a draft angle is the amount of taper, e.g., for molded or cast parts, perpendicular to the parting line. For example, as shown in FIG. 3A, a substantially rectangular channel 110, which has walls 112-A and 112-B that are substantially perpendicular to surface 114 (e.g., a parting line), has a draft angle 116 of 0°. The cross sections of fluidic channels having non-zero draft angles, on the other hand, may resemble a triangle, a parallelogram, a trapezoid, etc. For example, as shown in the embodiment illustrated in FIG. 3B, channel 120 has a substantially triangular cross-section. Draft angle 116 is formed by the angle between a line perpendicular to surface 114 and wall 127-A of the channel, and is non-zero in this embodiment.

The draft angle of an optical element, channel, or other component may be, for example, between about 1° and about 40°, between about 1° and about 30°, between about 1° and about 20°, between about 1° and about 10°, between about 2° and about 15°, between about 3° and about 10°, or between about 3° and about 8°. For instance, the draft angle may be greater than or equal to about 1°, 2°, 3°, 4°, 5°, 6°, 7°, 8°, 9°, or 10°, 20°, 37.5°, or 40°. In some cases, it is desirable for optical elements or channels to have specific draft angles so that they are compatible with a certain detection technique.

As described herein, optical elements may be combined with a fluidic device comprising one or more meandering channels. As shown in a top view of the illustrative embodiment of FIG. 3C, channel 208 includes a meandering (e.g., serpentine) region having a tightly packed channel system having a series of turns 210 and channel segments 212 that span over a large area (A) relative to the width of the channel. The area spanned by the meandering channel (i.e., the area of the meandering region) is the area bound by outermost points of the meandering channel along each axis, shown approximately in FIG. 3C by the dashed lines. This area may constitute a measurement area over which a detector may be positioned, the measurement area including both channel segments 212 and intervening channel portions 220 (i.e., non-channel segments).

FIG. 3C also shows plurality of optical elements 236 interspersed between the channel segments at the intervening channel portions 220. One measurement area may include, for example, greater than or equal to 3, 5, 8, 10, 15, 20, 30, 40, or 50 optical elements. The optical elements may be the same or different from one another, and may have any suitable shape or size as described herein. Furthermore, as illustrated, a fluidic device may include optical elements that extend past the measurement area and/or past the channel segments. This configuration may allow control of light even at turns 210 of the channel segments.

As shown in FIG. 3C, the length of channel segments 212-A and 212-C are the same. In other embodiments, however, the lengths of the segments of the meandering channel vary within the channel. Channel segments having different lengths may result in a measurement area having different shapes. The meandering channel (and the area of the channel) can be designed to have any suitable shape, e.g., a square, rectangular, circular, oval, triangular, spiral, or an irregular shape, since in certain cases the overall shape does not affect the fluid flow conditions within the channel.

In FIG. 3C, the area (A) that the meandering channel spans is defined by the surface area given by dimension B times (x) dimension C. Typically, the area spanned by the channel (i.e., as viewed from above the channel, perpendicular to the direction of fluid flow) is on the order of millimeters squared ($mm^2$). For instance, the area may be greater than or equal to 0.5 $mm^2$, greater than or equal to 1 $mm^2$, greater than or equal to 2 $mm^2$, greater than or equal to 5 $mm^2$, greater than or equal to 10 $mm^2$, or greater than or equal to 50 $mm^2$. However, in other embodiments, e.g., depending on the method used for detection, the area spanned by a meandering channel may be between 0.25 $mm^2$ and 0.5 $mm^2$, or between 0.1 $mm^2$ and 0.25 $mm^2$. Typically, the area spanned by the meandering channel is designed to be relatively large (e.g., on the order of $mm^2$) compared to conventional microfluidic systems, so that a wide area can be used for detection and so the total amount of signal that can be detected is increased, especially in combination with one or more optical elements described herein.

In some embodiments, the optical elements described herein are integral to a surface of the article. As used herein, "integral" refers to a condition of being a single, unitary construction, as opposed to separate parts that are connected by other means. For instance, integral optical elements of article may be formed in a surface of the article. Integral optical elements may be either concave or convex relative to the surface on which they are formed. For example, optical elements 32 and 34 in FIGS. 1A-1B are shown as concave optical elements integral to surface 16. In some cases, such optical elements, or molds for the optical elements, are fabricated using an photolithography process, e.g., as shown in FIGS. 4A-4B and as described in more detail below.

As shown in various embodiments herein, one or more optical elements may be positioned substantially between two channel segments and/or one or more channel segments may be positioned substantially between two optical elements. A first object is said to be positioned "substantially between" second and third other objects when substantially all of the first object lies between the center planes of the second and third objects. As used herein, a "center plane" of an object refers to an imaginary plane that intersects the geometric center of the cross section of the object and is substantially perpendicular to the substrate in or on which the object is positioned or formed. The term "geometric center" (or "centroid") is given its normal meaning in the art. For example, in FIG. 1A, channels 26, 28, and 30 comprise center planes 26', 28', and 30', which intersect geometric centers 26", 28" and 30", respectively. In addition, optical elements 32 and 34 comprise center planes 32' and 34' which intersect geometric centers 32" and 34", respectively. Optical element 32 is positioned substantially between channels 26 and 28, and optical element 34 is positioned substantially between channels 28 and 30. Channel segment 28 is positioned substantially between optical elements 32 and 34.

In some embodiments, one or more optical elements of a device lie on a substantially different plane than one or more channels of the device. For example, in FIG. 1A, the plane 60 intersecting the central axes of the optical elements (positioned at the geometric centers and extending out of and into the page) does not intersect the plane 62 intersecting the central axes of the channels. In some embodiments, no line drawn between any first point on or within a first microfluidic channel segment and any second point on or within a second microfluidic channel segment intersects any point on or within an optical element. In some instances, no line drawn between any first point on or within a first optical element and any second point on or within a second optical element intersects any point on or within a microfluidic channel segment.

In other embodiments, however, all or a portion of an optical element lies on the same plane as one or more channel or channel segment. For instance, an optical element may be formed in or on the same surface as the channels. In another example, an optical element is formed on a side opposite a channel, but extends such that a plane perpendicular to the surface of the article passes through both the channel and the optical element. In some cases, a line drawn between a first point on or within a first channel segment and a second point on or within a second channel segment intersects a point on or within the optical element.

Fluidic devices described herein comprising optical elements may be optionally combined with other features (e.g., certain detection systems, lenses, etc.) for reducing the amount of stray light and/or for increasing the signal to noise ratio. FIGS. 5-10 show various examples of detection systems and results of experiments performed when such systems were used in combination with devices described herein. In some cases, however, these features may be implemented independently of the optical elements described herein.

In some embodiments, additional techniques may be employed that compensate for the transmission of stray light through the microfluidic device. For example, the size (e.g., width, surface area, volume) of the intervening portions in the system may be reduced, thus reducing the percentage of light incident on the intervening portions. It should be noted that while it may not be practical to eliminate the intervening portions between the channels, as discussed in International Patent Publication No. WO2006/113727, thinner intervening portions and/or wider fluidic channels may result in less stray light transmitted and, therefore, improved performance.

The effects of reducing the size of the intervening portions on the amount of transmitted stray light can be evaluated by measuring transmission or absorbance in the system when the microchannels are filled with a perfectly absorbent fluid. Transmission through such a system is calculated as:

$$Trans = \frac{I}{I_o} \quad [10]$$

where $I_o$ is the intensity of light transmitted with a perfectly clear (index matched) fluid in the channels, and I is the intensity of light transmitted with a perfectly absorbent fluid in the channel.

The optical density (OD) is a measure of absorbance in such a system, which is calculated as the negative log of transmission:

$$OD = -\log(Trans) \quad [11]$$

A system with a minimum amount of stray light transmissions results in a large OD. In theory, a measurement zone filled with a perfectly absorbent fluid and with no intervening portions and no stray light would have a transmission of 0% and very large OD. In practice, it is difficult to completely eliminate stray light in any system. A transmission measurement through an extremely absorbent fluid in a microwell (no walls, or even channels) might be 0.01%, yielding an OD of 4. In general, though, transmission measurements below 1% can be difficult to achieve. A reasonable range of ODs that may be achieved may be within the range of about 0 to about 2.

Assuming a perfectly absorbent fluid in the channels, the transmission through a meandering channel region (without optical elements to block or re-direct light) is simply a function of the width of the intervening portions and the width of the channel. For example, in a system with intervening portions with widths of x and channels with widths of y, the minimum transmission would be x/(x+y). In the case of a meandering channel with identical widths for all intervening portions and channels, the value of x/(x+y) is 50% (yielding a maximum OD of 0.3). Similarly, a system with channels twice the width of the intervening portions would yield a minimum transmission of 33% (a maximum OD of 0.477). There is an upper (and lower) range for the channel widths based on the flow required in the system, since an increase in width of the channel results in an increase in cross section and changes in the properties of the channels, such as a reduction in the resistance to flow. Likewise, there is a lower range at which intervening portions can be reliably fabricated (e.g., depending on the fabrication technique). Example 3 outlines a set of experiments in which the widths of the intervening portions were varied.

In some embodiments, a detection system includes measuring the light transmitted through the channel portions independently of the light transmitted through the intervening portions. For example, one may image the measurement area with a digital camera, measure the intensity of light on the pixels that correspond to the channels and discard the pixels corresponding to the channel walls or the intervening portions. Optionally, lenses may be incorporated to focus the image on the plane of the channels. Such a measurement system could potentially deliver extremely high performance (avoiding stray light) and yield maximum ODs greater than about 2, e.g., OD=2-4.

However, in some cases, including a camera/imaging system may result in a relatively high cost of the imaging device, relatively high cost of lenses, precision required in positioning and alignment, robustness to shock or environmental conditions, and implementation of software to identify which pixels are to be measured and which to be ignored. Accordingly, these factors may be weighed with their benefits and may be suitable for certain, but not all, applications.

In one embodiment, a relatively inexpensive and robust imaging system was developed for a channel system utilizing a linear image sensor. A linear image sensor is a one-dimensional array of multiple small optical detectors which can be individually measured. FIGS. 8A and 8B include schematic diagrams of exemplary imaging systems used to measure transmission through meandering channels. The optical detector 810 in FIG. 8A is a single photodiode that may image a substantial portion of the meandering channel. In FIG. 8B, on the other hand, the optical detector 812 comprises a linear image sensor that measures only portions of the meandering channel. Optionally, optical components such as a collimating lens for the light source and/or a focusing lens to transmit the image to the linear image sensor (not shown) may be utilized to improve imaging. FIG. 8C includes a micrograph of a meandering channel used in one set of embodiments. A typical measurement area for a linear image sensor is indicated as region 820. In certain devices, each optical detector of a linear image sensor can be measured individually. Such a system can be used to measure transmission through only a portion of a system. For example, a linear image sensor located under a meandering channel region as shown in FIG. 8C can be used to measure light transmission only through the channels. To do this, only the readings from detectors under the channels are recorded. Other detectors positioned under non-channel portions (e.g., intervening portions) and struck by stray light can be ignored. In this manner, linear image sensors can be used to selectively measure light transmission through channels in a meandering channel region, eliminating the problem of stray light, and yielding accurate transmission/absorbance measurements for the microfluidic system.

Examples of linear image sensors include the Hamamatsu 59227, a 6.4 mm long array of 512, 250-micron wide pixels at 12.5 micron spacing, the Fairchild Imaging CMOS 1421, a 14.5 mm-long array of 2048, 7-micron wide pixels with 7 um center-to-center spacing, and the Panavision SVI LIS-500, a 3.9 mm long array of 500, 62.5-wide pixels with 7.8 um center-to-center spacing. Example 4 outlines the use of a linear image sensor in conjunction with the devices and methods described herein.

In some cases, the system may be designed to eliminate potential stray light before it reaches the fluidic device. For example, stray light may be eliminated by creating a light source that includes a geometry that matches the pattern of channel(s), directing light only onto the channels and away from the channel walls or intervening portions.

A variety of determination (e.g., measuring, quantifying, detecting, and qualifying) techniques may be used with devices described herein. Determination techniques may include optically-based techniques such as light transmission, light absorbance, light scattering, light reflection as well as luminescence techniques such as photoluminescence (e.g., fluorescence), chemiluminescence, bioluminescence, and/or electrochemiluminescence. Those of ordinary skill in the art know how to modify microfluidic devices in accordance with the determination technique used. For instance, for devices including chemiluminescent species used for determination, an opaque and/or dark background may be preferred. For determination using metal colloids, a transparent background may be preferred. Furthermore, any suitable detector may be used with devices described herein. For example, simplified optical detectors, as well as conventional spectrophotometers and optical readers (e.g., 96-well plate readers) can be used.

When more than one chemical and/or biological reaction (e.g., a multiplex assay) is performed on a device, the signal acquisition can be carried out by moving a detector over each analysis region. In an alternative approach, a single detector can detect signal(s) in each of the analysis regions simultaneously. In another embodiment, an analyzer can include, for example, a number of parallel optical sensors/detectors, each aligned with a analysis region and connected to the electronics of a reader. Additional examples of detectors and detection methods are described in more detail in U.S. patent application Ser. No. 12/196,392, filed Aug. 22, 2008, entitled "Liquid containment for integrated assays", which is incorporated herein by reference.

As described herein, a meandering channel of an analysis region may be configured and arranged to align with a detector such that upon alignment, the detector can measure a single signal through more than one adjacent channel segments of the meandering channel. In some embodiments, the detector is able to detect a signal within at least a portion of the area of the meandering channel and through more than one segments of the meandering channel such that a first portion of the signal, measured from a first segment of the meandering channel, is similar to a second portion of the signal, measured from a second segment of the meandering channel. In such embodiments, because the signal is present as a part of more than one segment of the meandering channel, there is no need for precise alignment between a detector and an analysis region.

Additional examples and descriptions of detection systems are provided in the Examples section.

In some embodiments, the fluidic devices described herein include a reaction site in fluid communication with one or more channels or channel segments. For example, the fluidic device may comprise a reaction site comprising a binding partner (e.g., an antibody, antigen, etc.) associated with a surface of a channel segment. An entity in the fluid flowing in the channel segment may interact (e.g., bind, chemically react, etc.) with the binding partner, and the interaction may be optically detectable.

In one set of embodiments, a fluidic device described herein is used for performing an immunoassay. The immunoassay may be, for example, a direct immunoassay, a sandwich (e.g., 2-site) immunoassay, or a competitive immunoassay, as known to those of ordinary skill in the art. Certain devices may include a combination of one or more such immunoassays.

In one particular embodiment, a fluidic device is used for performing an immunoassay (e.g., for human IgG or PSA) and, optionally, uses sliver enhancement for signal amplification. A device described herein may have one or more similar characteristics as those described in U.S. patent application Ser. No. 12/113,503, filed May 1, 2008 and entitled "Fluidic Connectors and Microfluidic Systems", which is incorporated herein by reference. In such an immunoassay, after delivery of a sample containing human IgG to a reaction area or analysis region, binding between the human IgG and anti-human IgG can take place. One or more reagents, which may be optionally stored in the device prior to use, can then flow over this binding pair complex. One of the stored reagents may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone), which can optionally be stored in different channels prior to use.

As a positive or negative pressure differential is applied to the system, the silver salt and hydroquinone solutions can merge at a channel intersection, where they mix (e.g., due to diffusion) in a channel, and then flow over the analysis region. Therefore, if antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. Any opaque layer that is formed in the microfluidic channel can be detected optically, for example, by measuring a reduction in light transmittance through a portion of the analysis region (e.g., a meandering channel region) compared to a portion of an area that does not include the antibody or antigen. Alternatively, a signal can be obtained by measuring the variation of light transmittance as a function of time, as the film is being formed in a analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

It should be understood that devices described herein may be used for any suitable chemical and/or biological reaction, and may include, for example, other solid-phase assays that involve affinity reaction between proteins or other biomolecules (e.g., DNA, RNA, carbohydrates), or non-naturally occurring molecules. In some embodiments, a chemical and/or biological reaction involves binding. Different types of binding may take place in devices described herein. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

Non-limiting examples of analytes that can be determined using fluidic devices described herein include specific proteins, viruses, hormones, drugs, nucleic acids and polysaccharides; specifically antibodies, e.g., IgD, IgG, IgM or IgA immunoglobulins to HTLV-I, HIV, Hepatitis A, B and non A/non B, Rubella, Measles, Human Parvovirus B19, Mumps, Malaria, Chicken Pox or Leukemia; human and animal hormones, e.g., thyroid stimulating hormone (TSH), thyroxine (T4), luteinizing hormone (LH), follicle-stimulating hormones (FSH), testosterone, progesterone, human chorionic gonadotropin, estradiol; other proteins or peptides, e.g. troponin I, c-reactive protein, myoglobin, brain natriuretic protein, prostate specific antigen (PSA), free-PSA, complexed-PSA, pro-PSA, EPCA-2, PCADM-1, ABCA5, hK2, beta-MSP (PSP94), AZGP1, Annexin A3, PSCA, PSMA, JM27, PAP; drugs, e.g., paracetamol or theophylline; marker nucleic acids, e.g., PCA3, TMPRS-ERG; polysaccharides such as cell surface antigens for HLA tissue typing and bacterial cell wall material. Chemicals that may be detected include explosives such as TNT, nerve agents, and environmentally hazardous compounds such as polychlorinated biphenyls (PCBs), dioxins, hydrocarbons and MTBE. Typical sample fluids include physiological fluids such as human or animal whole blood, blood serum, blood plasma, semen, tears, urine, sweat, saliva, cerebro-spinal fluid, vaginal secretions; in-vitro fluids used in research or environmental fluids such as aqueous liquids suspected of being contaminated by the analyte. In some embodiments, one or more of the above-mentioned reagents is stored in a channel or chamber of a fluidic device prior to first use in order to perform a specific test or assay.

Some embodiments of the invention are in the form of a kit that may include, for example, a microfluidic system, a source for promoting fluid flow (e.g., a vacuum), and/or one, several, or all the reagents necessary to perform an analysis except for the sample to be tested. In some embodiments, the microfluidic system of the kit may have a configuration similar to one or more of those shown in the figures and/or as described herein. The fluidic device of the kit may be portable and may have dimensions suitable for use in point-of-care settings.

The kit may include reagents and/or fluids that may be provided in any suitable form, for example, as liquid solutions or as dried powders. In some embodiments, a reagent is stored in the microfluidic system prior to first use, as described in more detail herein. When the reagents are provided as a dry powder, the reagent may be reconstituted by the addition of a suitable solvent, which may also be provided. In embodiments where liquid forms of the reagent are provided, the liquid form may be concentrated or ready to use. The fluids may be provided as specific volumes (or may include instructions for forming solutions having a specific volume) to be flowed in the microfluidic system.

The kit may be designed to perform a particular analysis such as the determination of a specific disease condition. For instance, markers (e.g., PSA) for specific diseases (e.g., prostate cancer) may be included (e.g., stored) in a device or kit in a fluid or dry form prior to first use of the device/kit. In order to perform a particular analysis or test using the kit, the fluidic device may be designed to have certain geometries, and the particular compositions, volumes, and viscosities of fluids may be chosen so as to provide optimal conditions for performing the analysis in the system. For example, if a reaction to be performed at an analysis region requires the flow of an amplification reagent over the analysis region for a specific, pre-calculated amount of time in order produce an optimal signal, the fluidic device may be designed to include a channel segment having a particular cross-sectional area and length to be used with a fluid of specific volume and viscosity in order to regulate fluid flow in a predetermined and pre-calculated manner. Washing solutions and buffers may also be included. The device may optionally include one or more reagents stored therein prior to first use. Furthermore, the kit may include a device or component for promoting fluid flow, such as a source of vacuum dimensioned to be connected to an outlet. The device or component may include one or more pre-set values so as to create a known (and optionally constant) pressure drop between an inlet and an outlet of the fluidic device. Thus, the kit can allow one or more reagents to flow for a known, pre-calculated amount of time at an analysis region, or at other regions of the system, during use. Those of ordinary skill in the art can calculate and determine the parameters necessary to regulate fluid flow using general knowledge in the art in combination with the description provided herein.

A kit described herein may further include a set of instructions for use of the kit. The instructions can define a component of instructional utility (e.g., directions, guides, warnings, labels, notes, FAQs ("frequently asked questions"), etc., and typically involve written instructions on or associated with the components and/or with the packaging of the components for use of the microfluidic system. Instructions can also include instructional communications in any form (e.g., oral, electronic, digital, optical, visual, etc.), provided in any manner such that a user will clearly recognize that the instructions are to be associated with the components of the kit.

In some embodiments, microfluidic systems described herein contain stored reagents prior to first use of the device and/or prior to introduction of a sample into the device. In some cases, one or both of liquid and dry reagents may be stored on a single article. Additionally or alternatively, the reagents may also be stored in separate vessels such that a reagent is not in fluid communication with the microfluidic system prior to first use. The use of stored reagents can simplify use of the microfluidic system by a user, since this minimizes the number of steps the user has to perform in order to operate the device. This simplicity can allow microfluidic systems described herein to be used by untrained users, such as those in point-of-care settings, and in particular, for devices designed to perform immunoassays. It has been demonstrated previously that the storage of the reagents in the form of liquid plugs separated by air gaps were stable for extended periods of time (see, for example, International Patent Publication No. WO2005/072858 (International Patent Application Serial No. PCT/US2005/003514), filed Jan. 26, 2005 and entitled "Fluid Delivery System and Method," which his incorporated herein by reference in its entirety. Fluidic devices for storing reagents may also include a configuration as described in U.S. patent application Ser. No. 12/640,420 filed on Dec. 17, 2009 and entitled, "Improved Reagent Storage in Microfluidic Systems and Related Articles and Methods," which is incorporated herein by reference in its entirety. In other embodiments, however, microfluidic devices described herein do not contain stored reagents prior to first use of the device and/or prior to introduction of a sample into the device.

As used herein, "prior to first use" of the device means a time or times before the device is first used by an intended user after commercial sale. First use may include any step(s) requiring manipulation of the device by a user. For example, first use may involve one or more steps such as puncturing a sealed inlet to introduce a reagent into the device, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

The devices described herein may comprise one or more channels or channel segments. A "channel" or "channel portion", as used herein, means a feature on or in an article or substrate (e.g., formed in a surface/side of an article or substrate) that at least partially directs the flow of a fluid. A channel, channel portion, or channel segment, etc. can have any cross-sectional shape (circular, oval, triangular, irregular, square or rectangular, trapezoidal, or the like) and can be covered or uncovered. In embodiments where it is covered, at least one portion of the channel can have a cross-section that is substantially enclosed, or the entire channel may be substantially enclosed along its entire length with the exception of its inlet(s) and outlet(s). In some cases, the inlet and/or outlet may also be enclosed or sealed, e.g., to prevent fluids and/or other reagents from being removed from the device (e.g., due to evaporation).

A channel, channel segment, channel portion, etc., may also have an aspect ratio (length to average cross-sectional dimension) of at least 2:1, more typically at least 3:1, 5:1, or 10:1 or more. In some embodiments, one or more channels, channel segments, channel portions, intervening channels, etc., is microfluidic. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel" or "microfluidic channel segment" as used herein, is a channel meeting these criteria. Though in some embodiments, devices of the invention may be microfluidic, in certain embodiments, the invention is not limited to microfluidic systems and may relate to other types of fluidic systems. Furthermore, it should be understood that all or a majority of the channels described herein may be microfluidic in certain embodiments. The "cross-sectional dimension" (e.g., a diameter, a height, and/or a width) of a channel, channel segment, channel portion, or intervening channel, etc. is measured perpendicular to the direction of fluid flow. In one set of embodiments, the maximum cross-sectional dimension of one or more channels or channel segments containing embodiments described herein are less than about 750 microns, less than about 500 microns, less than about 300 microns, less than about 200 microns, less than about 100 microns, less than about 50 microns, less than about 25 microns, less than about 10 microns, or less than about 5 microns. In some cases, at least two cross-sectional dimensions (e.g., a height and a width) of a channel, channel segment, or channel portion have one or more of the dimensions listed above (e.g., a width of less than 500 microns and a height of less than 200 microns).

One or more channels or channel segments described herein may have any suitable length. In some cases, the channels or channel segments may be at least about 1 mm long, at least about 2 mm long, at least about 5 mm long, at least about 10 mm long, at least about 20 mm long, at least about 50 mm long, or longer.

The channels or channel segments may also be spaced any suitable distance apart from each other. For example, in some cases, the width of one or more intervening portions between channels or channel segments may be less than about 5 mm, less than about 2 mm, less than about 1 mm, less than about 500 microns, less than about 300 microns, less than about 200 microns, less than about 100 microns, less than about 50 microns, less than about 25 microns, less than about 10 microns, less than about 5 microns, or less. In certain embodiments, channel segments may be separated by a distance of less than 0.01 times, less than 0.1 times, less than 0.25 times, less than 0.5 times, less than 1 times, less than 2 times, less than 5 times, or less than 10 times the average largest width of the channel segment.

The channels or channel segments may also be oriented in any suitable manner. In some instances, all channels or channel segments are spaced a substantially equal distance from each other (i.e., the widths of the intervening portions are all substantially the same). The channels or channel segments may also be oriented such that two or more (e.g., all) are substantially parallel to each other.

In some cases the dimensions of a channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used.

In some embodiments described herein, microfluidic systems include only a single interconnected channel with, for example, less than 5, 4, 3, 2, or 1 channel intersection(s) when in use. A layout based on a single channel with minimal or no intersections may be reliable because there is only one possible flow path for any fluid to travel across the microfluidic chip.

A microfluidic system described herein may have any suitable volume for carrying out a chemical and/or biological reaction or other process. The entire volume of a microfluidic system includes, for example, any reagent storage areas, reaction areas, liquid containment regions, waste areas, as well as any fluid connectors, and microfluidic channels associated therewith. In some embodiments, small amounts of reagents and samples are used and the entire volume of the microfluidic system is, for example, less than 10 milliliters, less than 5 milliliters, less than 1 milliliter, less than 500 microliters, less than 250 microliters, less than 100 microliters, less than 50 microliters, less than 25 microliters, less than 10 microliters, less than 5 microliters, or less than 1 microliter.

A fluidic device and/or an article described herein may be portable and, in some embodiments, handheld. The length and/or width of the device and/or article may be, for example, less than or equal to 20 cm, 15 cm, 10 cm, 8 cm, 6 cm, or 5 cm. The thickness of the device and/or article may be, for example, less than or equal to 5 cm, 3 cm, 2 cm, 1 cm, 8 mm, 5 mm, 3 mm, 2 mm, or 1 mm. Advantageously, portable devices may be suitable for use in point-of-care settings.

All or a portion of a fluidic device such as an article or a cover can be fabricated of any suitable material. For example, articles that include channels may be formed of a suitable for forming a microchannel. Non-limiting examples of materials include polymers (e.g., polyethylene, polystyrene, polymethylmethacrylate, polycarbonate, poly(dimethylsiloxane), PTFE, PET, and a cyclo-olefin copolymer), glass, quartz, and silicon. The article and/or cover may be hard or flexible. Those of ordinary skill in the art can readily select a suitable material based upon e.g., its rigidity, its inertness to (e.g., freedom from degradation by) a fluid to be passed through it, its robustness at a temperature at which a particular device is to be used, its transparency/opacity to light (e.g., in the ultraviolet and visible regions), and/or the method used to fabricate features in the material. For instance, for injection molded or other extruded articles, the material used may include a thermoplastic (e.g., polypropylene, polycarbonate, chlorotrifluoroethylene, acrylonitrile-butadiene-styrene, nylon 6), an elastomer (e.g., polyisoprene, isobutene-isoprene, nitrile, neoprene, ethylene-propylene, hypalon, silicone), a thermoset (e.g., epoxy, unsaturated polyesters, phenolics), or combinations thereof. In some embodiments, the material and dimensions (e.g., thickness) of an article and/or cover are chosen such that it is substantially impermeable to water vapor. For instance, a fluidic device designed to store one or more fluids therein prior to first use may include a cover comprising a material known to provide a high vapor barrier, such as metal foil, certain polymers, certain ceramics and combinations thereof. In other cases, the material is chosen based at least in part on the shape and/or configuration of the device. For instance, certain materials can be used to form planar devices whereas other materials are more suitable for forming devices that are curved or irregularly shaped.

In some instances, a fluidic device is formed of a combination of two or more materials, such as the ones listed above. For instance, the channels of the device may be formed in a first material (e.g., poly(dimethylsiloxane)), and a cover that is formed in a second material (e.g., polystyrene) may be used to seal the channels. In another embodiment, a first set of channels is formed in a first article comprising a first material and a second set of channels is formed in a second article comprising a second material. In yet another embodiment, channels of the device may be formed in polystyrene or other polymers (e.g., by injection molding) and a biocompatible tape may be used to seal the channels. The biocompatible tape may include a material known to improve vapor barrier properties (e.g., metal foil, polymers or other materials known to have high vapor barriers). A variety of methods can be used to seal a microfluidic channel or portions of a channel, or to join multiple layers of a device, including but not limited to, the use of adhesives (such as acrylic or silicone based adhesives), use adhesive tapes, gluing, bonding, lamination of materials, or by mechanical methods (e.g., clamping).

Sealing a channel and/or any inlets and outlets may protect and retain any gases, liquids, and/or dry reagents that may be stored within a channel. In addition or alternatively to one or more covers described herein, in certain embodiments, a fluid having low volatility, such as an oil or glycol may be placed in the end of a tube to help prevent evaporation and/or movement of other fluids contained therein.

Devices comprising optical elements and channels (e.g., microchannels) described herein may be fabricated using a variety of techniques. For example, the devices described herein may be formed using injection molding, hot embossing, or other plastic engineering techniques. The devices may also be manufactured using traditional machining techniques. In some cases, the devices may be fabricated by producing a mold and transferring the features of the mold to a hardenable polymer (e.g., PDMS). Molds may be fabricated by, for example, etching features into a silicon wafer (e.g., via an anisotropic KOH etch) and transferring the features onto a hardenable material (e.g., SU-8) which may then serve as a mold. In some cases, the microfluidic devices described herein include an article that is a single, integral piece of material without joined layers.

In one set of embodiments, purely photolithographic techniques are used to fabricated the channels and optical elements in a polymer. FIGS. 4A-4B illustrate a fabrication process that may be used to produce triangular optical elements in photoresist. In FIG. 4A, a layer of photoresist 410 overlies substrate 412. Photomask 414, comprising UV-transparent feature 416, is exposed to ultraviolet light 418. The ultraviolet light is directed at an angle 420 from the normal of the photomask. The development of the photoresist layer results in the formation of a triangular feature 430, as shown in FIG. 4B. This technique may produce features having smooth surfaces. In addition, the technique may be used to fabricate features with a relatively wide range of draft angles (e.g., from about 0° to about 20°). Such methods are known to those of ordinary skill in the art.

The manufacturing processes used to produce devices by injection molding (or other plastic engineering techniques, such as hot embossing), often require molds having non-zero draft angles on some or all of the features to be replicated in plastic. As discussed above, a draft angle is the amount of taper for molded or cast parts perpendicular to the parting line (a square channel with walls perpendicular to the floor having a draft angle of zero degrees). A non-zero draft angle is often necessary to allow demolding of the replica from the molding tool.

The fabrication of elements with non-zero draft angles is challenging. For instance, for microfluidic structures (e.g., channels) having various depths, the corresponding mold must have features with multiple heights in addition to non-zero draft angles. These types of molds can be challenging to fabricate on the microscale, as molding microchannels in plastic with constrictions in draft angle, depth, as well as in width is not trivial.

In fact, few techniques can yield the appropriate shapes for a mold having non-zero draft angles. To widen the breadth of technologies able to produce the appropriate shapes, an indirect route to the fabrication of the mold can be chosen. For instance, the channels themselves can be created in various materials, by various techniques to produce a master. The negative shape of the master is then obtained (e.g., by electrodeposition), resulting in a mold for injection molding. The techniques capable of yielding a master with non-zero draft angles and various depths include: (1) milling with one or more trapezoidal-shaped bits, (2) photolithographic techniques in combination with thick photosensitive polymers, for instance photosensitive glass or photoresist like SU8, in combination with a backside exposure or a top-side exposure with light with a non-normal angle. An example of the use of non-normal top-side exposure with photosensitive glass to produce features with non-zero draft angles is described in U.S. Pat. No. 4,444,616. The preparation of multiple depths can be achieved by multiple photolithographic exposures onto multiple layers of photosensitive material. (3) KOH etching on silicon substrates can also produce non-zero draft angles, according to the crystalline planes of the silicon. (4) Alternative to straight draft angles, channels having rounded side-walls can also produce suitable master for molds. Such rounded side-walls can be achieved by isotropic etching onto planar surface (e.g., HF etching on Pyrex wafers), or by reflowing structures photoresist by heat treatment. (5) Deep Reactive Ion Etching (DRIE) can also produce non-zero degree draft angles under certain parameters.

The following examples are intended to illustrate certain embodiments of the present invention, but are not to be construed as limiting and do not exemplify the full scope of the invention.

EXAMPLE 1

Fabrication of Microfluidic Channels

A method for fabricating a microfluidic channel system is described.

Channel systems, such as the ones shown in FIGS. 1A and 1B, were designed with a computer-aided design (CAD) program. The microfluidic devices were formed in poly (dimethylsiloxane) Sylgard 184 (PDMS, Dow Corning, Ellsworth, Germantown, Wis.) by rapid prototyping using masters made in SU8 photoresist (MicroChem, Newton, Mass.). The masters were produced on a silicon wafer and were used to replicate the negative pattern in PDMS. The masters contained two levels of SU8, one level with a thickness (height) of ~70 μm defining the channels in the immunoassay area, and a second thickness (height) of ~360 μm defining the reagent storage and waste areas. Another master was designed with channel having a thickness (height) of 33 μm. The masters were silanized with (tridecafluoro-1,1,2,2-tetrahydrooctyl)trichlorosilane (ABC-R, Germany). PDMS was mixed according to the manufacturer's instructions and poured onto the masters. After polymerization (4 hours, 65° C.), the PDMS replica was peeled off the masters and access ports were punched out of the PDMS using stainless steel tubing with sharpened edges (1.5 mm in diameter). To complete the fluidic network, a flat substrate such as a glass slide, silicon wafer, polystyrene surface, flat slab of PDMS, or an adhesive tape was used as a cover and placed against the PDMS surface. The cover was held in place either by van der Waals forces, or fixed to the microfluidic device using an adhesive.

In other embodiments, the microfluidic channels were made in polystyrene or other thermoplastics by injection molding. This method is known to those of ordinary skill in the art. The volume of an injection molding cavity can be defined by a bottom surface and a top surface separated by a hollow frame which determines the thickness of the molded article. For an article including channel features and or other microscale elements on two opposing sides of the article, the bottom and top surfaces of the molding cavity may include raised features that create the channel features on either side of the article. For an article including channel features on only one side of the article, only the top or bottom surface of the molding cavity includes such features. Thru-holes that pass through the entire thickness of the article can be produced by pins traversing the cavity, embedded in one or more surfaces of the cavity and contacting the other side. For instance, the pins may extend from only the top surface, only the bottom surface, or from both the top and bottom surfaces.

EXAMPLE 2

Performance of a System Comprising Triangular Optical Elements

This example describes the transmission profiles of systems employing a meandering channel, one with triangular optical elements (grooves) and another without. An article was fabricated in polystyrene with identical systems of fluidic channels on one side. Some of these channels included triangular optical elements between the channels on the other side (shielded channels). Other channels did not include triangular optical elements between them (normal/ standard channels with no shielding). The channels were 160 microns in width. Intervening portions between the channels were 60 microns in width. The article thickness was designed using the model described above. Triangular optical elements were also designed as described in the model above with an angle of 35.3°, a width of 160 microns, and a pitch of 220 microns. Optical measurements were performed using a single collimated LED light source and a single photodiode detector.

Measurements were performed with an approximate index-matching liquid in the channels (water) and with a concentrated absorbing dye (Methylene Blue, 20 mg/ml in water). Using water in the "normal" channel (channel without optical elements) as the baseline, the following transmission measurements were made:

|  | Transmission | OD |
| --- | --- | --- |
| Water in Normal Channel | 100% | 0.00 |
| Dye in Normal Channel | 27% | 0.56 |
| Water Shielded Channel | 26% | 0.58 |
| Dye in Shielded Channel | 1% | 1.98 |

Assuming a perfectly absorbing dye, the transmission through normal channels should be 27%, since the channel walls make up 60/(60+160)=27% of the area of the measurement zone. Experimental results confirmed this prediction. Note that the range of ODs provided by a non-shielded channel of these dimensions would be 0 to 0.56. In shielded channels with dye, only 1% of the incident light was transmitted. The triangular optical element was designed to either block light that would be transmitted through the intervening portions or directed the light into the channels. The dye in the channels absorbed most, if not all, the light striking the channels.

With water in the shielded channels, 26% of the light incident on the measurement zone was transmitted. With a width 60 microns and a pitch of 220 microns, the triangular optical elements blocked 73% of the top surface of the measurement area. The remaining 27% of the area was positioned directly above channels. Since these channels were filled with index matching liquid, it was assumed that they transmitted all of the light striking them. A total transmission of 26% indicated that, in this particular experiment, significantly more of the light incident on the optical elements was reflected out of the system than was directed to the channels.

Figure 5:
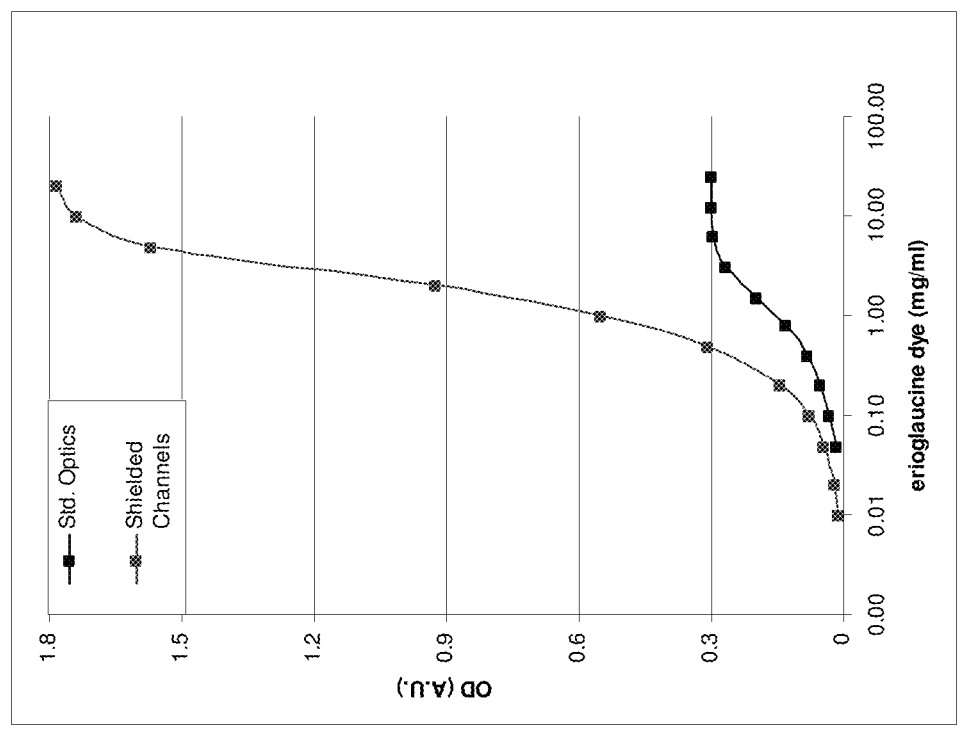
FIG. 5 includes a plot of optical density as a function of dye concentration, according to one set of embodiments.

To understand the measurement range of the shielded channels, a comparison was made between the intensity of light transmitted through the shielded channels with dye and the intensity of light transmitted through the shielded channels with water. Using the shielded channels with water as a baseline, the transmission with dye was 4%. This indicated that the range of ODs provided by the shielded system with channels of these dimensions would be 0 to 1.40. This represents a significant improvement over the normal configuration. FIG. 5 presents a comparison of ODs measured in shielded meandering channels and ODs measured in unshielded meandering channels. In this example, erioglaucine dye was used. As can be seen, the shielding delivered a larger dynamic range of ODs corresponding to superior performance.

Figure 6A:
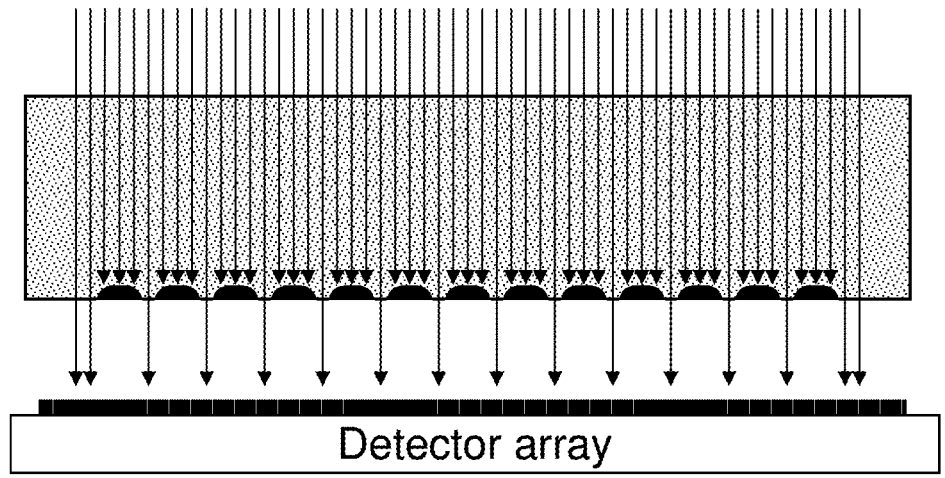
FIGS. 6A-6D include cross-sectional schematic diagrams and associated plots of transmitted light as a function of detector position, according to one set of embodiments.
Figure 6B:
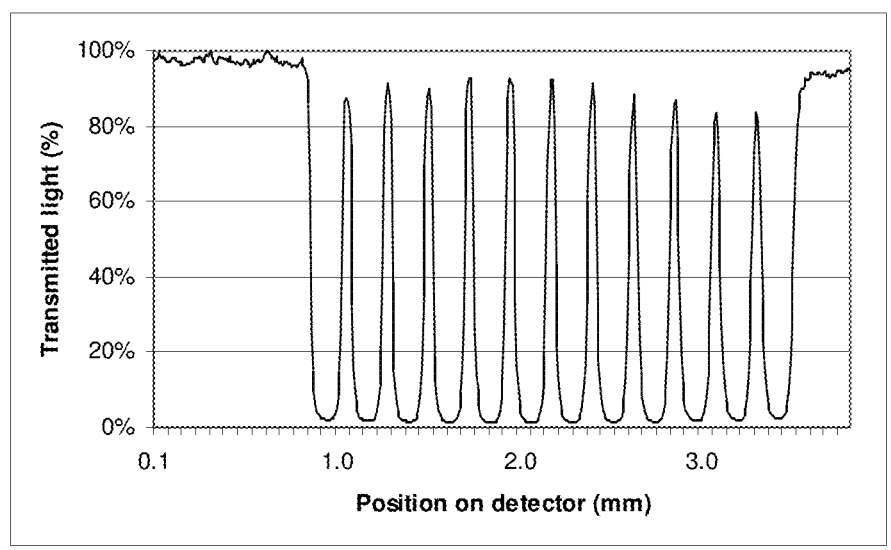

A more detailed comparison of transmitted light can be obtained using the linear image sensor system described above. FIG. 6A includes a schematic diagram outlining light transmission through a microfluidic meandering channel measurement zone without optical elements. In this set of experiments, the channels were filled with dark dye (10 mg/mL eriogalucine dye). A collimated light source was used to shine incident light onto the meandering channel measurement zone. A focusing lens and a linear image sensor was used to detect light through the measurement zone. The light incident upon the channels was absorbed by the dye, while the light incident between the channels passed through the article. FIG. 6B is a plot of the transmitted light as a function of position across the measurement zone. The peaks in FIG. 6B indicate the presence of a large amount of stray light between the channels.

Figure 6C:
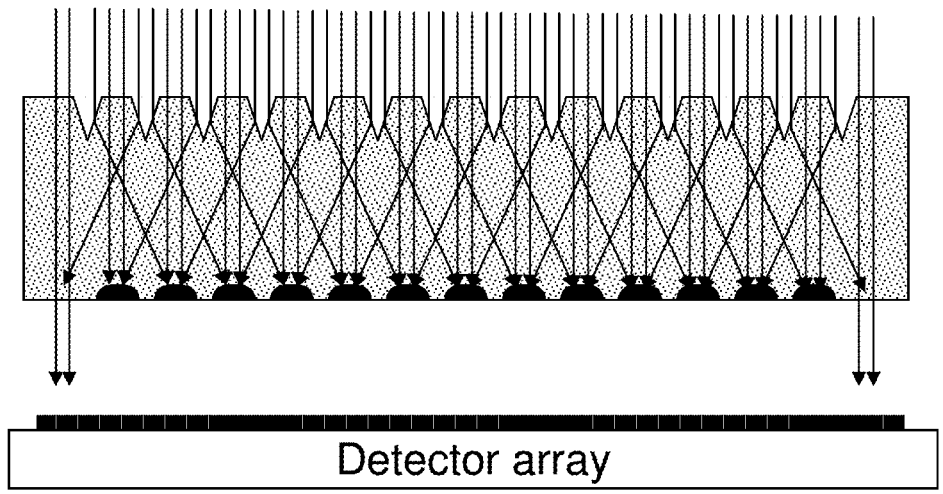
Figure 6D:
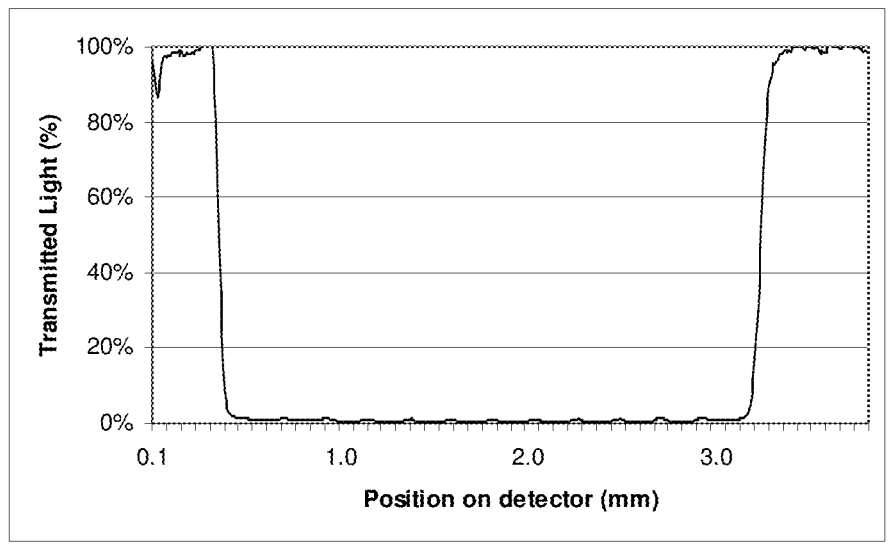

FIG. 6C includes a schematic diagram outlining light transmission through a microfluidic meandering channel measurement zone with optical elements. As in the previous set of experiments, the channels were filled with dye, which absorbed light incident upon the channels. FIG. 6D, like FIG. 6B, includes a plot of transmitted light as a function of position across the measurement zone. However, in this instance, the peaks corresponding to the positions between the channels have been reduced dramatically, meaning stray light between the channel reduced due to the presence of the optical elements. Due to the shielding provided by the optical elements, when they are employed, a single photosensor may provide nearly equivalent optical performance compared to a more complex linear image sensor. This shows that simplified optical systems can be used in combination with fluidic devices described herein.

EXAMPLE 3

Reducing the Width of Intervening Portions

Figure 7A:
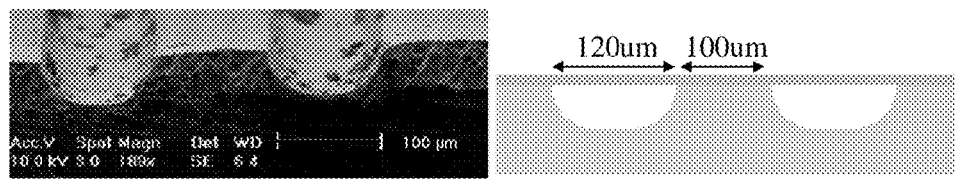
FIGS. 7A-7C include cross-sectional schematic diagrams, optical micrographs, and a plot of optical density as a function of dye concentration, according to one set of embodiments.
Figure 7B:
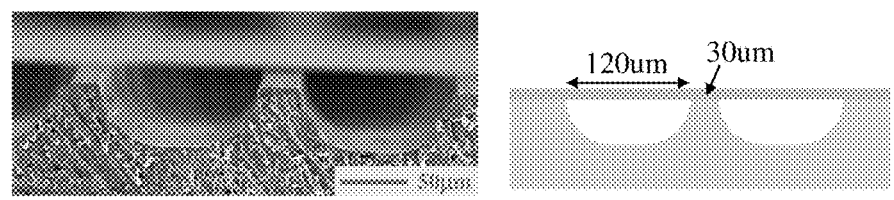
Figure 7C:
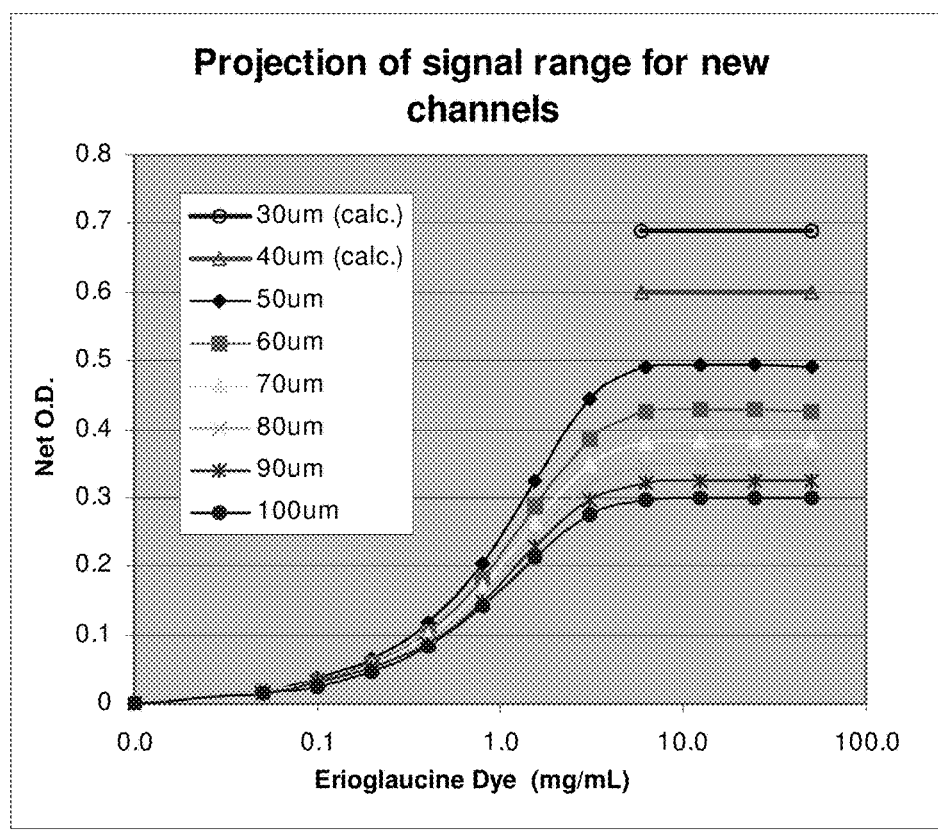

In this example, several samples with various widths of intervening portions were fabricated and tested. FIG. 7A includes a micrograph and a schematic illustration of a device comprising 120-micron-wide optical elements spaced 100 microns apart. In FIG. 7B, the optical elements are spaced only 30 microns apart. The channels were filled with dye (Erioglaucine) at various concentrations, and measurements of transmissions through the meandering channel region were taken. FIG. 7C includes a plot of the net OD as a function of the dye concentration for several devices including varied inter-element spacings. As can be seen from the plot, the OD increases with an increase in dye concentration and a decrease in inter-element spacing. Table 1 summarizes the theoretical maximum projected optical density (minimum transmission) and actual optical performance of these systems.

TABLE 1

Predicted and measured maximum optical densities for various devices.

| Channel width | Width of Intervening Portions | Predicted Max OD | Measured Max OD |
|---|---|---|---|
| 120 µm | 50 µm | 0.53 | 0.49 |
| 120 µm | 60 µm | 0.48 | 0.43 |
| 120 µm | 70 µm | 0.43 | 0.38 |
| 120 µm | 80 µm | 0.40 | 0.35 |
| 120 µm | 90 µm | 0.37 | 0.32 |
| 120 µm | 100 µm | 0.34 | 0.30 |

EXAMPLE 4

Use of Linear Image Sensors

This example describes the use of a linear image sensor in conjunction with the systems and methods described herein.

A linear image sensor was positioned underneath a meandering channel as shown in FIG. 8B such that detection elements were positioned below the surface including the channel. A focusing lens was mounted between the sensor and the meandering channel so that a focused image of the channel was projected onto the sensor surface. Collimated light was used to illuminate the meandering channel. In an alternative experimental setup, the linear image sensor was placed immediately underneath the meandering channel (i.e., within less than 0.5 mm), alleviating the need for a lens to be placed between the meandering channel and the surface of the optical detector.

Figure 9A:
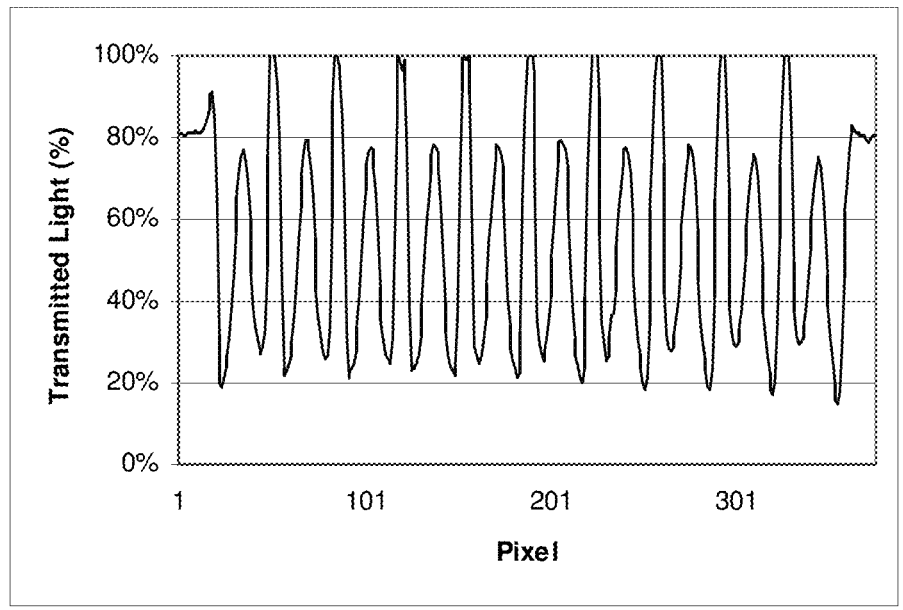
FIGS. 9A-9D include plots of transmitted light as a function of sensor position, according to one set of embodiments.
Figure 9B:
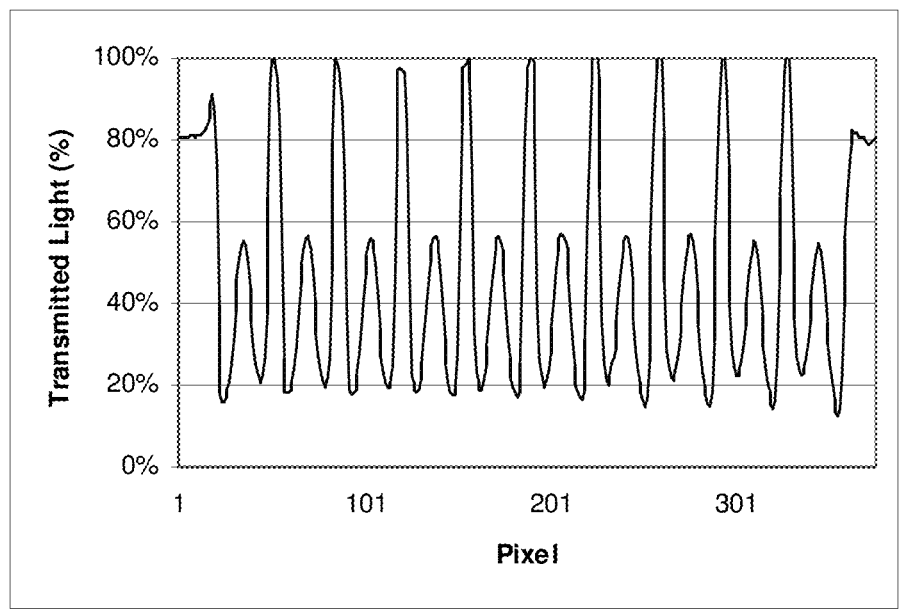
Figure 9C:
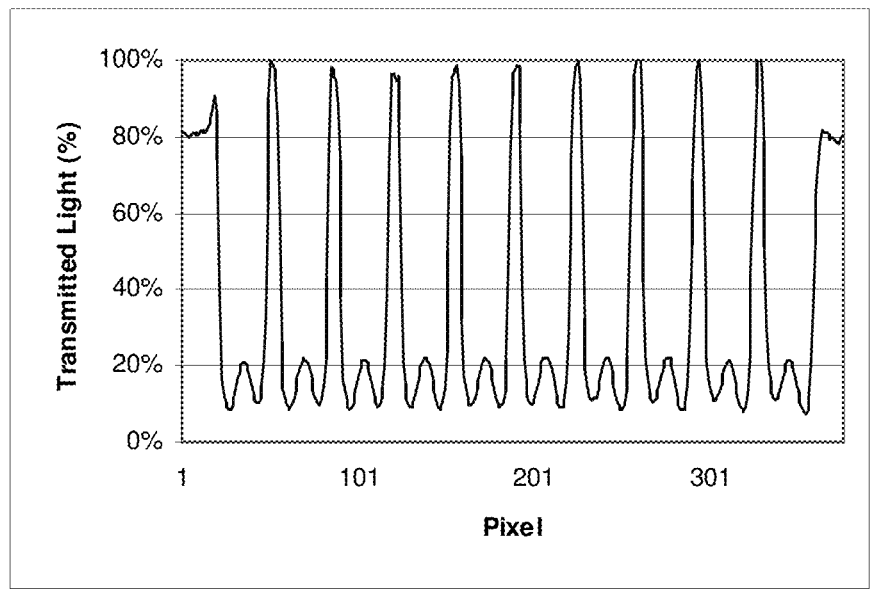
Figure 9D:
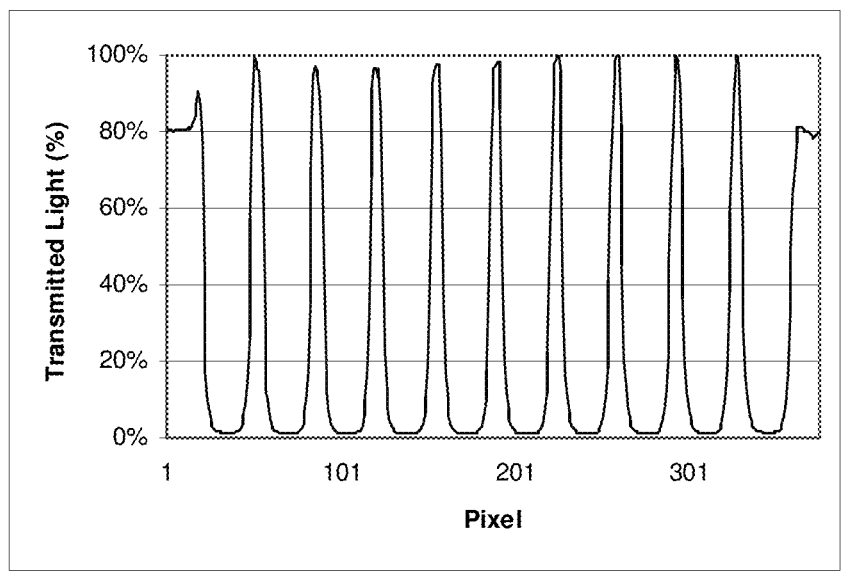

Measurements of the system were performed with various fluids in the channel including index-matching liquid, dye diluted in water, and concentrated dye. FIGS. 9A-9D include plots of transmitted light as a function of position along the linear image sensor for various dye concentrations. In FIG. 9A, a low dye concentration (0.05 mg/mL erioglaucine) was used in the channel. FIGS. 9B-9D show dye concentrations of 0.4 mg/mL, 1.6 mg/mL, and 50 mg/mL respectively. Less light was transmitted through the channels (i.e., absorbance increased) as the dye concentration increased. A software program was written to identify which pixels corresponded to positions within the channel. Selecting only these pixels, transmission was calculated as:

$$T = \frac{\text{Intensity of light detected with target liquid channel}}{\text{Intensity of light detected with index matching liquid in channel}} \quad [12]$$

A total transmission value was calculated by averaging the measurements from all the identified channel pixels.

Figure 10:
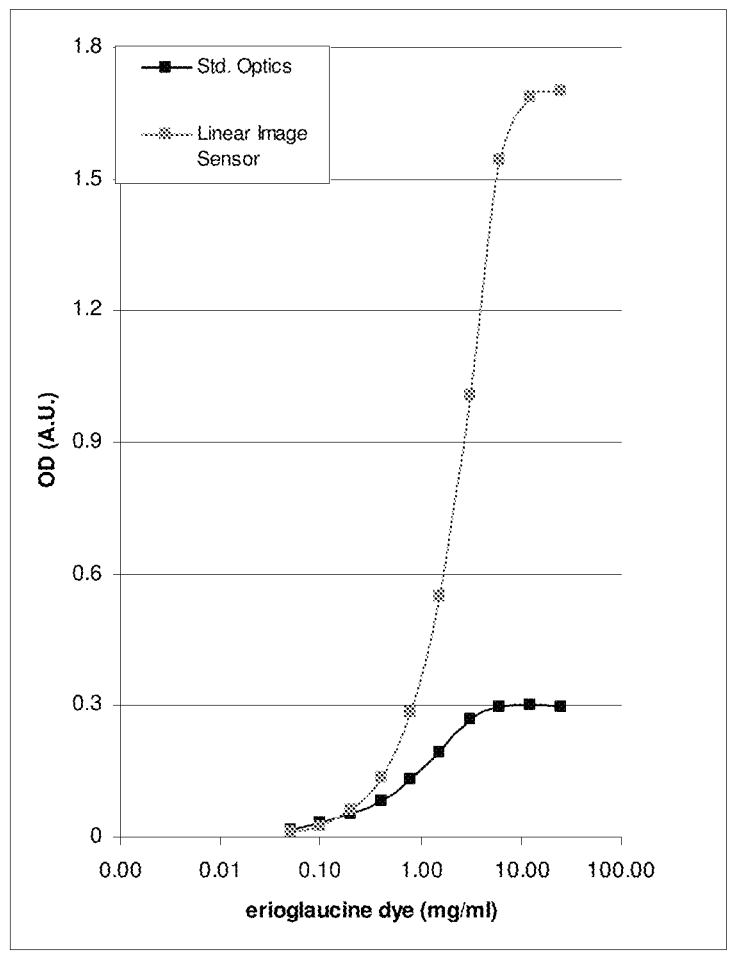
FIG. 10 includes a plot of optical density as a function of dye concentration, according to one set of embodiments.

Various concentrations of dyes were imaged in the channels (corresponding to various levels of absorption in the channels). Transmissions were calculated using the method explained above and converted into ODs. FIG. 10 includes plots of OD as a function of dye concentration when using a single photodetector (measuring the light traveling throughout the channels and between the channels) and when using a linear image sensor (discriminating pixels). The linear image sensor delivered a larger dynamic range of ODs corresponding to superior performance.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A multiplex assay system comprising:
   an article supporting solid-phase assays, said article comprising a rigid planar substrate and comprising two or more different liquid containment regions, each liquid containment region comprising at least one analysis region that can be interrogated optically, each analysis region having one or more binding partners associated with a surface of the substrate, wherein said binding partners hind one or more analytes present in a sample in the liquid containment region, and wherein, for at least one liquid containment region, the one or more analytes is selected from the group consisting of prostate specific antigen (PSA), free PSA, complexed-PSA, pro-PSA, and human kallikrein protein (hk2); and
   an optical device configured to supply collimated light to illuminate an analysis region of the two or more liquid containment regions and detect light from the illuminated analysis region.

2. The multiplex assay system of claim 1, wherein the one or more binding partner is an antibody.

3. The multiplex assay system of claim 1, wherein the sample is obtained from a whole blood, blood serum, or blood plasma sample.

4. The multiplex assay system of claim 1, wherein each different liquid containment region is a chamber having a depth measured perpendicular to a surface of the rigid planar substrate and a cross-sectional dimension substantially parallel to the surface of the rigid planar substrate.

5. The multiplex assay system of claim 4, wherein the chamber is integral to a surface of the rigid planar substrate.

6. The multiplex assay system of claim 4, wherein the chamber comprises a separate structure connected to the rigid planar substrate.

7. The multiplex assay system of claim 6, wherein the separate structure is connected to the rigid planar substrate through an adhesive and/or van der Waals forces.

8. The multiplex assay system of claim 7, wherein the adhesive is an acrylic or silicone based adhesive.

9. The multiplex assay system of claim 4, wherein the chamber is covered.

10. The multiplex assay system of claim 4, wherein the chamber is uncovered.

11. The multiplex assay system of claim 1, wherein each different liquid containment region is configured to contain less than 1 milliliter of liquid.

12. The multiplex assay system of claim 1, wherein the optical device further comprises a camera or imaging system.

13. The multiplex assay system of claim 1, wherein the optical device is configured to detect photoluminescence, fluorescence, chemiluminescence, bioluminescence, and/or electrochemiluminescence.

14. The multiplex assay system of claim 1, wherein the rigid planar substrate is a polyethylene, polystyrene, polymethylmethacrylate, polycarbonate, poly(dimethylsiloxane), polytetrafluoroethylene, polyethylene terephthalate, or cyclo-olefin copolymer substrate.

15. The multiplex assay system of claim 14, wherein the rigid planar substrate is a poly(dimethylsiloxane) substrate.

16. The multiplex assay system of claim 1, wherein the rigid planar substrate is a glass, quartz, or silicon substrate.

17. The multiplex assay system of claim 1, further comprising a second article comprising a rigid planar substrate comprising at least one analysis region in which one or more nucleic acid binding partners are associated with a surface of the substrate of the second article.

18. The multiplex assay system of claim 1, wherein the optical device further comprises a focusing lens to focus the light that illuminates the analysis region.

19. The multiplex assay system of claim 1, wherein the collimated light is supplied by directing light from a light source through a collimating lens.

20. A multiplex assay system comprising:
   an article supporting solid-phase assays, said article comprising a rigid planar substrate and comprising two or more different liquid containment regions, each liquid containment region comprising at least one analysis region that can be interrogated optically, each analysis region having one or more binding partners associated with a surface of the substrate, wherein said binding partners bind one or more analytes present in a sample in the liquid containment region, and wherein, for at least one liquid containment region, the one or more analytes is selected from the group consisting of prostate specific antigen (PSA), free PSA, complexed-PSA, pro-PSA, and human kallikrein protein (hk2); and an optical device configured to supply collimated light to illuminate an analysis region of the two or more liquid containment regions and detect light from the illuminated analysis region, wherein the rigid planar substrate is composed of glass, quartz, or silicon; and wherein the sample is obtained from a whole blood, blood serum, or blood plasma sample.

21. The multiplex assay system of claim 20, wherein the optical device further comprises a focusing lens to focus the light that illuminates the analysis region.

22. The multiplex assay system of claim 20, wherein the collimated light is supplied by directing light from a light source through a collimating lens.

23. The multiplex assay system of claim 1, wherein the supplied collimated light and the detected light from the illuminated analysis region travel along a common path.

24. The multiplex assay system of claim 20, wherein the supplied collimated light and the detected light from the illuminated analysis region travel along a common path.

25. The multiplex assay system of claim 1, wherein the one or more binding partner is an antibody, wherein the sample is obtained from a whole blood, blood serum, or blood plasma sample, and wherein the supplied collimated light and the detected light from the illuminated analysis region travel along a common path.

26. The multiplex assay system of claim 20, wherein the one or more binding partner is an antibody and wherein the supplied collimated light and the detected light from the illuminated analysis region travel along a common path.

27. The multiplex assay system of claim 1, wherein each different liquid containment region is a chamber having a depth measured perpendicular to a surface of the rigid planar substrate and a cross-sectional dimension substantially parallel to the surface of the rigid planar substrate, wherein the chamber comprises a separate structure connected to the rigid planar substrate, and wherein the separate structure is connected to the rigid planar substrate through an adhesive and/or van der Waals forces.

28. The multiplex assay system of claim 20, wherein each different liquid containment region is a chamber having a depth measured perpendicular to a surface of the rigid planar substrate and a cross-sectional dimension substantially parallel to the surface of the rigid planar substrate, wherein the chamber comprises a separate structure connected to the rigid planar substrate, and wherein the separate structure is connected to the rigid planar substrate through an adhesive and/or van der Waals forces.

29. The multiplex assay system of claim 1, wherein each different liquid containment region is a chamber having a depth measured perpendicular to a surface of the rigid planar substrate and a cross-sectional dimension substantially parallel to the surface of the rigid planar substrate, wherein the chamber is uncovered, and wherein the optical device is configured to detect photoluminescence, fluorescence, chemiluminescence, bioluminescence, and/or electrochemiluminescence.

30. The multiplex assay system of claim 20, wherein each different liquid containment region is a chamber having a depth measured perpendicular to a surface of the rigid planar substrate and a cross-sectional dimension substantially parallel to the surface of the rigid planar substrate, wherein the chamber is uncovered, and wherein the optical device is configured to detect photoluminescence, fluorescence, chemiluminescence, bioluminescence, and/or electrochemiluminescence.

31. The multiplex assay system of claim 1, wherein the collimated light is supplied by directing light from a light source through a collimating lens and wherein the supplied collimated light and the detected light from the illuminated analysis region travel along a common path.

32. The multiplex assay system of claim 20, wherein the collimated light is supplied by directing light from a light source through a collimating lens and wherein the supplied collimated light and the detected light from the illuminated analysis region travel along a common path.

* * * * *

UNITED STATES PATENT AND TRADEMARK OFFICE
CERTIFICATE OF CORRECTION

PATENT NO. : 9,827,564 B2
APPLICATION NO. : 15/196975
DATED : November 28, 2017
INVENTOR(S) : David Steinmiller et al.

It is certified that error appears in the above-identified patent and that said Letters Patent is hereby corrected as shown below:

In the Specification

At Column 12, Line 23 the formula should appear as $$\sigma_h = \left[\langle(z-z_m)^2\rangle\right]^{1/2} = \left[\frac{1}{A}\int_A (z-z_m)^2 dA\right]^{1/2}$$

At Column 16, Line 63 the numbers "59227" should read --S9227--.

In the Claims

At Column 29, Claim 1, Line 64 the word "hind" should read --bind--.

Signed and Sealed this
Twenty-seventh Day of February, 2018

Andrei Iancu
*Director of the United States Patent and Trademark Office*